(12) United States Patent
Jiang et al.

(10) Patent No.: US 7,893,107 B2
(45) Date of Patent: *Feb. 22, 2011

(54) THERAPEUTIC METHODS USING PROSTAGLANDIN EP₄ AGONIST COMPONENTS

(75) Inventors: Guang-Liang Jiang, Lake Forest, CA (US); Wha Bin Im, Irvine, CA (US); Larry A. Wheeler, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 587 days.

This patent is subject to a terminal disclaimer.

(21) Appl. No.: 11/291,694

(22) Filed: Nov. 30, 2005

(65) Prior Publication Data

US 2007/0123568 A1  May 31, 2007

(51) Int. Cl.
  *A61K 31/19* (2006.01)
(52) U.S. Cl. ...................................... 514/573; 514/443
(58) Field of Classification Search ........................ None
  See application file for complete search history.

(56) References Cited

U.S. PATENT DOCUMENTS

| | | | |
|---|---|---|---|
| 3,931,297 | A | 1/1976 | Crabbe |
| 4,117,014 | A | 9/1978 | Pernet et al. |
| 4,171,375 | A | 10/1979 | Caton et al. |
| 6,410,591 | B1 | 6/2002 | Burk et al. |
| 6,538,018 | B1 | 3/2003 | Burk et al. |
| 6,552,067 | B2 | 4/2003 | Cameron et al. |
| 6,586,468 | B1 | 7/2003 | Maruyama et al. |
| 6,610,719 | B2 | 8/2003 | Paralkar et al. |
| 6,670,485 | B2 | 12/2003 | Burk et al. |
| 6,747,037 | B1 | 6/2004 | Old et al. |
| 6,747,054 | B2 | 6/2004 | Cameron et al. |
| 6,875,787 | B2 | 4/2005 | Donde |
| 2003/0120079 | A1 | 6/2003 | Elworthy et al. |
| 2003/0207925 | A1 | 11/2003 | Cameron et al. |
| 2004/0142969 | A1 | 7/2004 | Elworthy |
| 2004/0157901 | A1 | 8/2004 | Donde |
| 2005/0020686 | A1 | 1/2005 | Maruyama et al. |
| 2005/0124577 | A1 | 6/2005 | Tani et al. |

FOREIGN PATENT DOCUMENTS

| | | |
|---|---|---|
| BE | 850348 | 7/1977 |
| DE | 2701455 | 1/1977 |
| DE | 2752523 | 6/1978 |
| ES | 409167 | 11/1975 |
| FR | 2162213 | 12/1972 |
| FR | 2338244 | 1/1977 |
| FR | 2408567 | 11/1978 |
| GB | 1405301 | 11/1975 |
| JP | 52-097144 | 7/1977 |
| JP | 53-065854 | 6/1978 |
| JP | 63002972 | 1/1988 |
| NL | 7700272 | 1/1977 |
| SE | 7700257 | 7/1977 |
| WO | WO02/24647 | 3/2002 |
| WO | WO02/42268 | 5/2002 |
| WO | WO03/008377 | 1/2003 |
| WO | WO 03/008377 | 1/2003 |
| WO | WO03/009872 | 2/2003 |
| WO | WO 03/035064 | 5/2003 |
| WO | WO03/053923 | 7/2003 |
| WO | WO 03/053923 | 7/2003 |
| WO | WO03/074483 | 9/2003 |
| WO | WO03/077910 | 9/2003 |
| WO | WO03/103604 | 12/2003 |
| WO | WO 03/103604 | 12/2003 |
| WO | WO03/103664 | 12/2003 |
| WO | WO 03/103664 | 12/2003 |
| WO | WO 2004/019938 | 3/2004 |
| WO | WO 2004/037786 | 5/2004 |
| WO | WO 2004/037813 | 5/2004 |
| WO | WO 2004/065365 | 8/2004 |
| WO | WO 2004/078103 | 9/2004 |

OTHER PUBLICATIONS

Fries et al., Arthritis & Rheumatism, 50/8 (Aug. 2004), pp. 2433-2440.*
Friend and Chang, "A Colon-Specific Drug-Delivery System Based on Drug Glycosides and the Glycosidases of Colonic Bacteria", *J. Med. Chem.* 1984, 27, 261-266.
Friend and Chang, "Drug Glycosides: Potential Prodrugs for Colon-Specific Drug Delivery", *J. Med. Chem.* 1985, 28, 51-57.
Haeberlin et. al., "In Vitro Evaluation of Dexametnasone-β-D-Glucuronide for Colon-Specific Drug Delivery", *Pharmaceutical Research* 1993, 10, 1553-1562.
Hamon, A., et al., Synthesis of (+–)- and 15-EPI(+–)-10,10-Dimetnylprostaglandin E1, *Tetrahedron Letters*, Elsevier Science Publishers, Amsterdam, NL, No. 3, Jan. 1976, pp. 211-214.
Hirayama et al., "In-vitro Evaluation of Biphenyl Acetic Acid-β-Cyclodextrin Conjugates as Colon-targeting Prodrugs: Drug Release Behaviour in Rat Biological Media", *J. Pharm. Pharacol.* 1996, 48, 27-31.
Kabashima, et. al., "The prostaglandin receptor EP4 suppresses colitis, mucosal damage and CD4 cell activation in the gut", *The Journal of Clinical Investigation*, Apr. 2002, vol. 109, No. 7, 883-893.
McLeod et. al., "Synthesis and chemical stability of glucocorticoid-dextran esters: potential prodrugs for colon-specific delivery", *Int J. Pharm.* 1993, 92, 105-114.

(Continued)

*Primary Examiner*—Phyllis G. Spivack
(74) *Attorney, Agent, or Firm*—Kevin J. Forrestal; John E. Wurst; Doina G. Ene

(57) ABSTRACT

Methods are provided directed to administering a therapeutically effective amount of a prostaglandin EP₄ agonist component to a mammal afflicted with or prone to afflicted with a disease or condition selected from an esophageal ulcer, alcohol gastropathy, a duodenal ulcer, non-steroidal anti-inflammatory drug-induced gastropathy, non-steroidal anti-inflammatory drug-induced enteropathy and intestinal ischemia. Such administration results in treating the disease or condition.

10 Claims, No Drawings

OTHER PUBLICATIONS

Nakamura et. al., Development of a Prodrug of Salicylic Acid, Salicylic Acid-L-alanine Conjugate, Utilizing Hydrolysis by Rabbit Intestinal Microorganisms, *J. Pharm. Pharmacol.* 1992, 44, 295-299.

Nakamura et. al., "Hydrolysis of salicylic acid-tyrosine and salicylic acid-methionine prodrugs in the rabbit", *Int. J. Pharm.* 1992, 87, 59-66.

Northey, A., et al., "Cellular distribution of prostanoid EP receptors mRNA in the rat gastrointestinal tract", *Prostaglandins Other Lipid Mediat.* Jul. 2000;62(2):145-56.

Pernet, Andre G. et al., Prostaglandin analogs modified at the 10 and 11 positions, *Tetrahedron Letters*, (41), 1979, pp. 3933-3936.

Pelletier S., et al., "Prostaglandin E(2) increases cyclic AMP and inhibits endothelin-1 production/secretion by guinea-pig tracheal epithelial cells through EP(4) receptors", *Br J Pharmacol.* Mar. 2001;132(5):999-1008.

Planterna, Otto G. et al., Synthesis of($\pm$)-10.10-dimethylprostaglandin $E_1$ methyl ester and its 15-epimer, *Journal of the Chemical Society*, Perkin Transactions 1: Organic and Bio-organic Chemistry (1972-1999), (3), 1978, pp. 304-308.

Plantema, O. G. et al., Synthesis of 10,10-dimethyiprostaglandins[1], *Tetrahedron Letters*, No. 34: 1975, pp. 2945-2948, Pergamon Press. Printed in Great Britain.

Savla U., et al., "Prostaglandin $E_2$ regulates wound closure in airway epithelium", *Am. J. Physiol. Lung Cell Mol. Physiol.*, 2001:280(3):L421-431.

Takafuji, V., et al., "Prostanoid receptors in intestinal eptithelium: selective expression, function, and change with inflammation", *Prostaglandins Leukot Essent Fatt. Acids*, 2000;63(4):223-35.

Tanaka et. al., "Synthesis of Doxorubicin-Cyclodextrin Conjugates", *Journal of Antibiotics* 1994, 47, 1025-1029.

Uekama et al., "$6^A$-O-[4-Biphenylyl)acetyl]-$\alpha$-,-$\beta$-, and—$\gamma$-cyclodextrins and $6^A$-Deoxy-$6^A$-[[(4-biphenylyl)acetyl]amino]-$\alpha$-, -$\beta$-, $\gamma$-cyclodextrins: Potential Prodrugs for Colon-Specific Delivery", *J. Med. Chem.* 1997, 40, 2755-2761.

Houchen et al., "Prosurvival and antiapoptotic effects of $PGE_2$ in radiation injury are mediated by $EP_2$ receptor in intestine," Am J Ph siol Gastrointest Liver Physiol 284: G490-G498, 2003.

Hamann, et al., "An Anti-CD33 Antibody-Calicheamicin Conjugate for Treatment of Acute Myeloid Leukemia," Choide of Linker, Bioconjugate Chem. 2002,13, 40-46.

Plantema, et al., "Synthesis of 10, 10-Dimethylprostaglandins," Tetrahedron Letters No. 34, 1975, 2945-29485, 28, 51-57.

Jiang, et al., "The Prevention of Colitis by E Prostanoid Receptor 4 Agonist Through Enhancement of Epithelium Survival and Regeneration," The Jornal of Pharmacology, 2007, 320:22-28.

Jiang, et al., "The Prevention of Colitis by E Prostanoid Receptor 4 Agonist Through Enhacement of Epithelium Survival and Regeneration," The Journal of Pharmacology, 2007, 320:22-28, 2007.

* cited by examiner

US 7,893,107 B2

THERAPEUTIC METHODS USING PROSTAGLANDIN EP$_4$ AGONIST COMPONENTS

FIELD OF THE INVENTION

This invention relates to treating or preventing certain diseases or conditions using therapeutically active compounds. Particularly, this invention relates to methods using prostaglandin EP$_4$ agonist components to treat or prevent certain diseases or conditions.

BACKGROUND OF THE INVENTION

Description of Related Art

Prostaglandins can be described as derivatives of prostanoic acid which have the following structural formula:

Various types of prostaglandins are known, depending on the structure and substituents carried on the alicyclic ring of the prostanoic acid skeleton.

Further classification is based on the number of unsaturated bonds in the side chain indicated by numerical subscripts after the generic type of prostaglandin [e.g. prostaglandin E$_1$ (PGE$_1$), prostaglandin E$_2$ (PGE$_2$)], and on the configuration of the substituents on the alicyclic ring indicated by α or β [e.g. prostaglandin F$_{2\alpha}$ (PGF$_{2\beta}$)].

Certain 10,10-dimethyl prostaglandins are known. These are described in documents such as the following:

Donde, in United States Patent No. Patent Application Publication No. 20040157901;

Pernet et al in U.S. Pat. No. 4,117,014;

Pernet, Andre G. et al., Prostaglandin analogs modified at the 10 and 11 positions, Tetrahedron Letters, (41), 1979, pp. 3933-3936;

Plantema, Otto G. et al., Synthesis of (.+−.)-10.10-dimethylprostaglandin E1 methyl ester and its 15-epimer, Journal of the Chemical Society, Perkin Transactions 1: Organic and Bio-organic Chemistry (1972-1999), (3), 1978, pp. 304-308;

Plantema, O. G. et al., Synthesis of 10,10-dimethylprostaglandin E1, Tetrahedron Letters, (51), 1975, 4039;

Hamon, A., et al., Synthesis of (+−)- and 15-EPI(+−)-10,10-Dimethylprostaglandin E1, Tetrahedron Letters, Elsevier Science Publishers, Amsterdam, NL, no. 3, January 1976, pp. 211-214; and Patent Abstracts of Japan, Vol. 0082, no. 18 (C-503), Jun. 10, 1988 & JP 63 002972 A (Nippon Iyakuhin Kogyo KK), 7 Jan. 1988;

the disclosures of these documents are hereby expressly incorporated by reference.

United States Patent Application Publication 2004/0142969 A1, expressly incorporated by reference herein, discloses compounds according to the formula below The application discloses the identity of the groups as follows:

m is from 1 to 4; n is from 0 to 4; A is alkyl, aryl, heteroaryl, arylalkyl, arylcycloalkyl, cycloalkylalkyl, or aryloxyalkyl; E is —CHOH— or —C(O)—; X is —(CH$_2$)$_2$— or —CH=CH—; Y is —CH$_2$—, arylene, heteroarylene, —CH=CH—, —O—, —S(O)$_p$— where p is from 0 to 2, or —NR$^a$— where R$^a$ is hydrogen or alkyl; Z is —CH$_2$OH, —CHO, tetrazol-5-yl, or —COOR$^b$ where R$^b$ is hydrogen or alkyl; and R$^1$, R$^2$, R$^3$, R$^4$, R$^5$, R$^6$, R$^7$, R$^8$, R$^9$ and R$^{10}$ each independently are hydrogen or alkyl.

U.S. Pat. No. 6,747,037, expressly incorporated by reference herein, discloses prostaglandin EP$_4$ agonists such as U.S. Pat. No. 6,610,719, expressly incorporated by reference herein, discloses prostaglandin EP$_4$ selective agonists having the structure The patent describes the identity of the groups as follows:
Q is COOR$^3$, CONHR$^4$ or tetrazol-5-yl;
A is a single or cis double bond;
B is a single or trans double bond;
U is R$^2$ is α-thienyl, phenyl, phenoxy, monosubstituted phenyl or monosubstituted phenoxy, said substituents being selected from the group consisting of chloro, fluoro, phenyl, methoxy, trifluoromethyl and (C$_1$-C$_3$)alkyl;

$R^3$ is hydrogen, $(C_1-C_5)$alkyl, phenyl or p-biphenyl;
$R^4$ is $COR^5$ or $SO_2R^5$; and
$R^5$ is phenyl or $(C_1-C_5)$alkyl.

10-Hydroxyprostaglandin analogues, that is natural prostaglandin $EP_4$ agonist compounds where the hydroxide is present on carbon 10 rather than carbon 11, are known in several patent documents including U.S. Pat. No. 4,171,375; U.S. Pat. No. 3,931,297; FR 2408567; DE 2752523, JP 53065854, DE 2701455, SE 7700257, DK 7700272, NL 7700272, JP 52087144, BE 850348, FR 2338244, FR 2162213, GB 1405301, and ES 409167; all of which are expressly incorporated by reference herein.

U.S. patent application Ser. No. 821,705, filed Apr. 9, 2004, expressly incorporated by reference herein, discloses compounds having the following structure

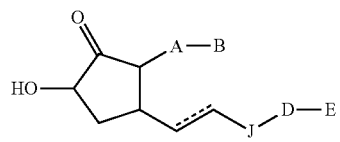

wherein
J is C=O or CHOH;
A is —$(CH_2)_6$—, or cis —$CH_2CH=CH—(CH_2)_3$—, wherein 1 or 2 carbons may be substituted with S or O;
B is $CO_2H$, or $CO_2R$, $CONR_2$, $CONHCH_2CH_2OH$, $CON(CH_2CH_2OH)_2$, $CH_2OR$, $P(O)(OR)_2$, $CONRSO_2R$, $SONR_2$, or

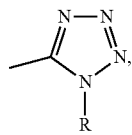

each of R and $R_2$ is independently H or $C_{1-6}$ alkyl;
D is —$(CH_2)_n$—, —$X(CH_2)_n$, or —$(CH_2)_nX$—, wherein n is from 0 to 3 and X is S or O; and
E is an aromatic or heteroaromatic moiety having from 0 to 4 substituents, said substituents each comprising from 1 to 6 non-hydrogen atoms as disclosed in the application.

Other compounds of interest are disclosed in U.S. Pat. No. 6,670,485; U.S. Pat. No. 6,410,591; U.S. Pat. No. 6,538,018; WO 2004/065365; WO 03/074483; WO 03/009872; WO 2004/019938; WO 03/103664; WO 2004/037786; WO 2004/037813; WO 03/103604; WO 03/077910; WO 02/42268; WO 03/008377 WO 03/053923; WO 2004/078103; and WO 2003/035064, all of which are expressly incorporated by reference herein.

Prostaglandin $EP_4$ selective agonists are believed to have several medical uses. For example, U.S. Pat. No. 6,552,067 B2, expressly incorporated by reference herein, teaches the use of prostaglandin $EP_4$ selective agonists for the treatment of "methods of treating conditions which present with low bone mass, particularly osteoporosis, frailty, an osteoporotic fracture, a bone defect, childhood idiopathic bone loss, alveolar bone loss, mandibular bone loss, bone fracture, osteotomy, bone loss associated with periodontitis, or prosthetic ingrowth in a mammal."

U.S. Pat. No. 6,586,468 B1, expressly incorporated by reference herein, teaches that prostaglandin $EP_4$ selective agonists "are useful for the prophylaxis and/or treatment of immune diseases (autoimmune diseases (amyotrophic lateral sclerosis (ALS), multiple sclerosis, Sjoegren's syndrome, arthritis, rheumatoid arthritis, systemic lupus erythematosus, etc.), post-transplantation graft rejection, etc.), asthma, abnormal bone formation, neurocyte death, pulmopathy, hepatopathy, acute hepatitis, nephritis, renal insufficiency, hypertension, myocardial ischemia, systemic inflammatory syndrome, pain induced by ambustion, sepsis, hemophagocytosis syndrome, macrophage activation syndrome, Still's diseases, Kawasaki diseases, burns, systemic granuloma, ulcerative colititis, Crohn's diseases, hypercytokinemia at dialysis, multiple organ failure, shock, etc."

Inflammatory bowel disease (IBD) is a group of diseases characterized by inflammation in the large or small intestines and is manifest in symptoms such as diarrhea, pain, and weight loss. Nonsteroidal anti-inflammatory drugs have been shown to be associated with the risk of developing IBD, and recently Kabashima and colleagues have disclosed that "$EP_4$ works to keep mucosal integrity, to suppress the innate immunity, and to downregulate the proliferation and activation of CD4+ T cells. These findings have not only elucidated the mechanisms of IBD by NSAIDs, but also indicated the therapeutic potential of $EP_4$-selective agonists in prevention and treatment of IBD." (Kabashima, et. al., *The Journal of Clinical Investigation*, April 2002, Vol. 9, 883-893).

Various other diseases or conditions of the mammalian body occur to the detriment of the individual affected. Among such diseases or conditions are esophageal ulcers, alcohol gastropathy, duodenal ulcers, non-steroidal anti-inflammatory drug-induced gastroenteropathy and intestinal ischemia. New methods for treating or preventing such diseases or conditions would be highly beneficial.

SUMMARY OF THE INVENTION

The present invention relates to methods of treating or preventing one or more diseases or conditions, for example, of the mammalian body. Treating or preventing such disease(s) or condition(s) provides one or more substantial advantages, for example, enhances or maintains the health status of the individual, for example, human or animal, afflicted with or prone to affliction with such disease(s) or condition(s). The present methods are relatively easy to practice.

In one broad aspect of the invention, the present methods comprise administering a therapeutically effective amount of a prostaglandin $EP_4$ agonist component to a mammal afflicted with or prone to affliction with one or more diseases or conditions selected from an esophageal ulcer, alcohol gastropathy, a duodenal ulcer, non-steroidal anti-inflammatory drug-induced gastroenteropathy and intestinal ischemia, thereby treating or preventing the one or more diseases or conditions.

In one embodiment, the prostaglandin $EP_4$ agonist component is administered to a human. The prostaglandin $EP_4$ agonist component may be administered, for example, directly administered, to the gastrointestinal tract of a mammal, for example, a human.

Any and all features described herein and combinations of such features are included within the scope of the present invention provided that the features of any such combination are not mutually inconsistent.

DETAILED DESCRIPTION

A prostaglandin $EP_4$ agonist is broadly defined as a compound which an ordinary person in the art reasonably believes agonizes a prostaglandin $EP_4$ receptor according to any one or more of numerous assays for determination of the $EP_4$ activity that are well known to those of ordinary skill in the art. While not intending to be limiting, one such assay is given hereinafter.

In one embodiment, the prostaglandin $EP_4$ agonist is selective for a prostaglandin $EP_4$ receptor relative to other prostaglandin receptor subtypes. In another embodiment, the prostaglandin $EP_4$ agonist is at least 10 times more active at the $EP_4$ receptor than at any other prostaglandin receptor subtype. In another embodiment, the prostaglandin $EP_4$ agonist is at least 100 times more active at the $EP_4$ receptor than at any other prostaglandin receptor subtype. In another embodiment, the prostaglandin $EP_4$ agonist is at least 1000 times more active at the $EP_4$ receptor than at any other prostaglandin receptor subtype. While not intending to be limiting, typical assays for the other receptor subtypes are also given hereinafter.

While not intending to limit the scope of the invention in any way, compounds according to the structures below are examples of prostaglandin $EP_4$ agonists or prostaglandin $EP_4$ agonist components:

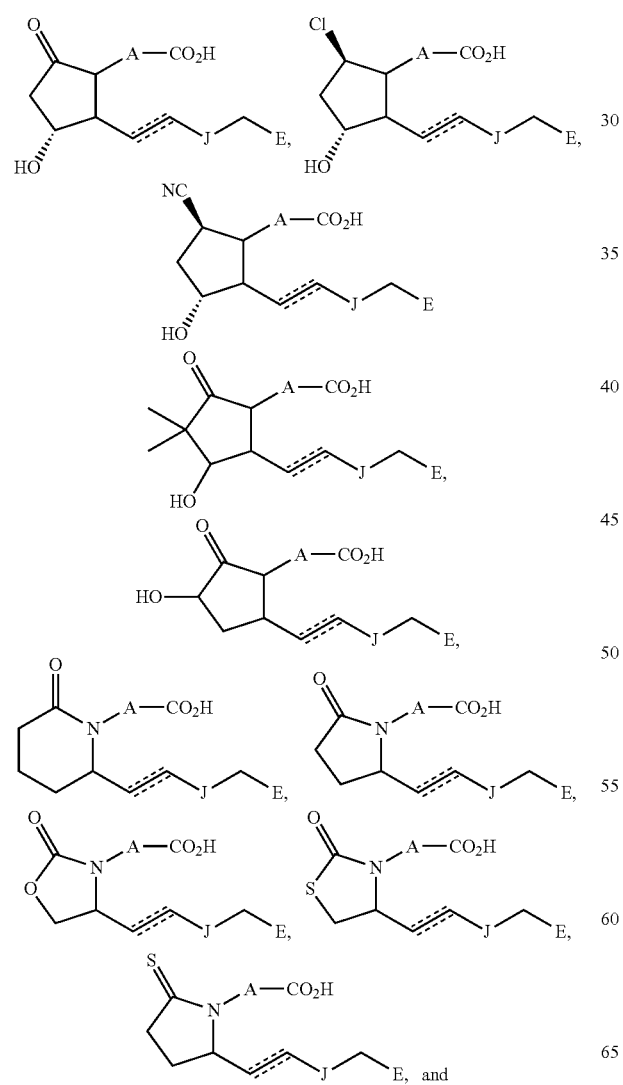

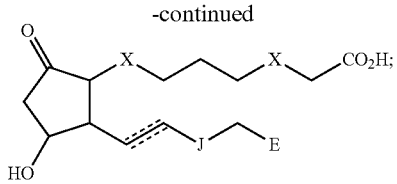

-continued pharmaceutically acceptable salts thereof; and prodrugs thereof, wherein a dashed line represents the presence of absence of a bond;

A is $-(CH_2)_6-$, cis $-CH_2CH=CH-(CH_2)_3-$, or $-CH_2C\equiv C-(CH_2)_3-$, wherein 1 or 2 carbon atoms may be substituted with S or O; or A is $-(CH_2)_m-Ar-(CH_2)_o-$ wherein Ar is interarylene or heterointerarylene, the sum of m and o is from 1 to 4, and wherein one $CH_2$ may be substituted with S or O;

X is S or O;

J is C=O, CHOH, or $CH_2$CHOH; and

E is $C_{1-12}$ alkyl, $R^2$, or $-Y-R^2$ wherein Y is $CH_2$, S, or O, and $R^2$ is aryl or heteroaryl.

In these structures, a dashed line represents the presence or absence of a bond. Thus, a structure such as the one below,

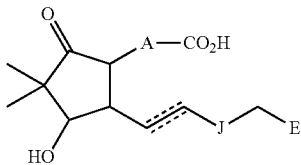

represents three different structures, depicted as follows.

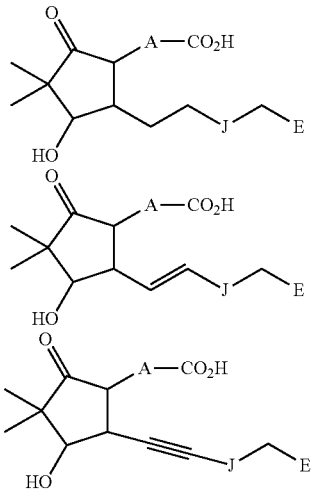

In relation to the identity of A disclosed in the chemical structures presented herein, in the broadest sense, A is $-(CH_2)_6-$, cis $-CH_2CH=CH-(CH_2)_3-$, or $-CH_2C\equiv C-(CH_2)_3-$, wherein 1 or 2 carbon atoms may be substituted with S or O; or A is $-(CH_2)_m-Ar-(CH_2)_o-$ wherein Ar is interarylene or heterointerarylene, the sum of m and o is from 1 to 3, and wherein one $CH_2$ may be substituted with S or O.

While not intending to be limiting, A may be —(CH$_2$)$_6$—, cis —CH$_2$CH=CH—(CH$_2$)$_3$—, or —CH$_2$C≡C—(CH$_2$)$_3$—.

Alternatively, A may be a group which is related to one of these three moieties in which any carbon is substituted with S and/or O. For example, while not intending to limit the scope of the invention in any way, A may be an S substituted moiety such as one of the following or the like.

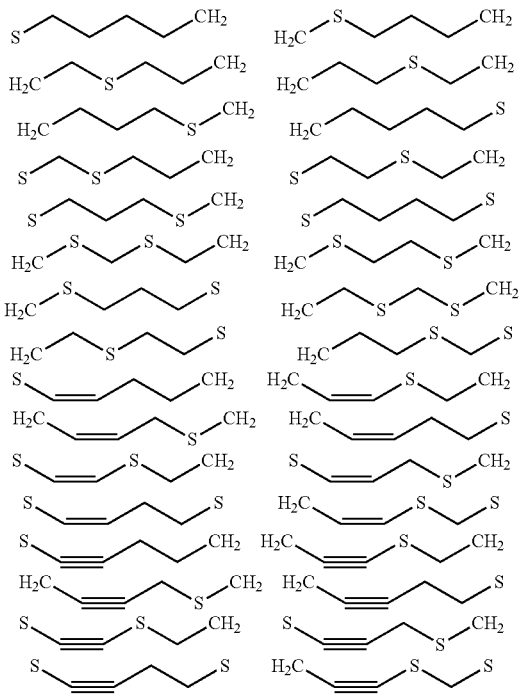

Alternatively, while not intending to limit the scope of the invention in any way, A may be an O substituted moiety such as one of the following or the like.

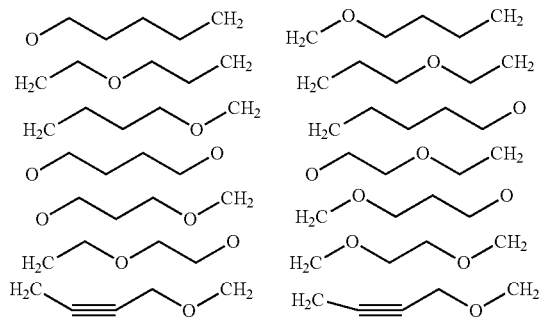

Alternatively, while not intending to limit the scope of the invention in any way, A may have both an O and a S substituted into the chain, such as one of the following or the like.

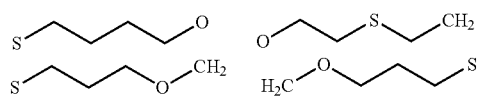

Alternatively, while not intending to limit the scope of the invention in any way, in certain embodiments A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O. In other words, while not intending to limit the scope of the invention in any way, in one embodiment A comprises from 1 to 4 CH$_2$ moieties and Ar, e.g. —CH$_2$—Ar—, —(CH$_2$)$_2$—Ar—, —CH$_2$—ArCH$_2$—, —CH$_2$Ar(CH$_2$)$_2$—, —(CH$_2$)$_2$—Ar(CH$_2$)$_2$—, and the like; or A comprises O, from 0 to 3 CH$_2$ moieties, and Ar, e.g., —O—Ar—, Ar—CH$_2$—O—, —O—Ar—(CH$_2$)$_2$—, —O—CH$_2$—Ar—, —O—CH$_2$—Ar—(CH$_2$)$_2$, and the like; or A comprises S, from 0 to 3 CH$_2$ moieties, and Ar, e.g., —S—Ar—, Ar—CH$_2$—S—, —S—Ar—(CH$_2$)$_2$—, —S—CH$_2$—Ar—, —S—CH$_2$—Ar—(CH$_2$)$_2$, and the like.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Thus, an unsubstituted interarylene has 4 potential positions where a substituent could be attached. In one embodiment, Ar is substituted or unsubstituted interphenylene, interthienylene, interfurylene, or interpyridinylene. In one embodiment Ar is interphenylene (Ph). In one embodiment A is —(CH$_2$)$_2$-Ph-. While not intending to limit the scope of the invention in any way, substituents may have 4 or less heavy atoms, or in other words, non-hydrogen atoms. Any number of hydrogen atoms required for a particular substituent will also be included. Thus, the substituent may be hydrocarbyl having up to 4 carbon atoms, including alkyl up to C$_4$, alkenyl, alkynyl, and the like; hydrocarbyloxy up to C$_3$; CF$_3$; halo, such as F, Cl, or Br; hydroxyl; NH$_2$ and alkylamine functional groups up to C$_3$; other N or S containing substituents; and the like.

In one embodiment A is —(CH$_2$)$_m$—Ar—(CH$_2$)$_o$— wherein Ar is interphenylene, the sum of m and o is from 1 to 3, and wherein one CH$_2$ may be substituted with S or O.

In another embodiment A is —CH$_2$—Ar—OCH$_2$—. In another embodiment A is —CH$_2$—Ar—OCH$_2$— and Ar is interphenylene. In another embodiment, Ar is attached at the 1 and 3 positions, such as when A has the structure shown below.

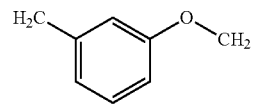

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_2$-Ph- wherein one CH$_2$ may be substituted with S or O.

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_2$-Ph-.

J is C=O, CHOH, or CH$_2$CHOH. Thus, while not intending to limit the scope of the invention in any way, compounds such as the ones below are useful as prostaglandin EP$_4$ agonists.

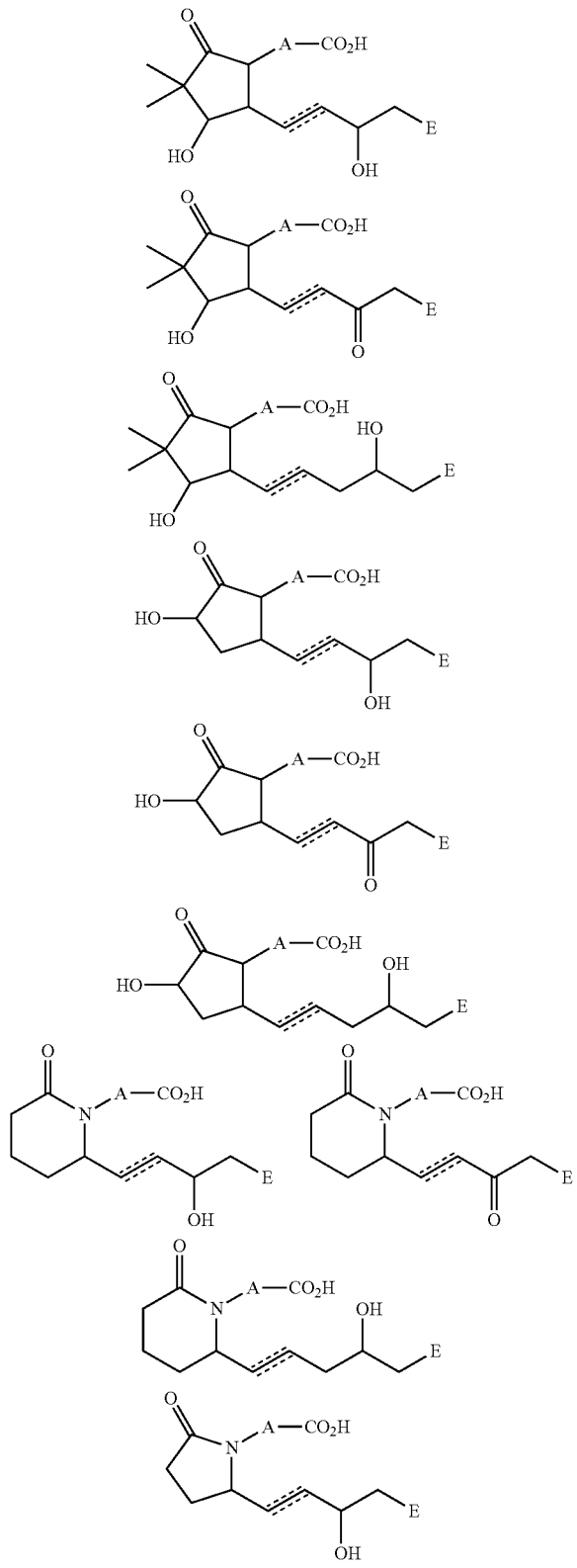

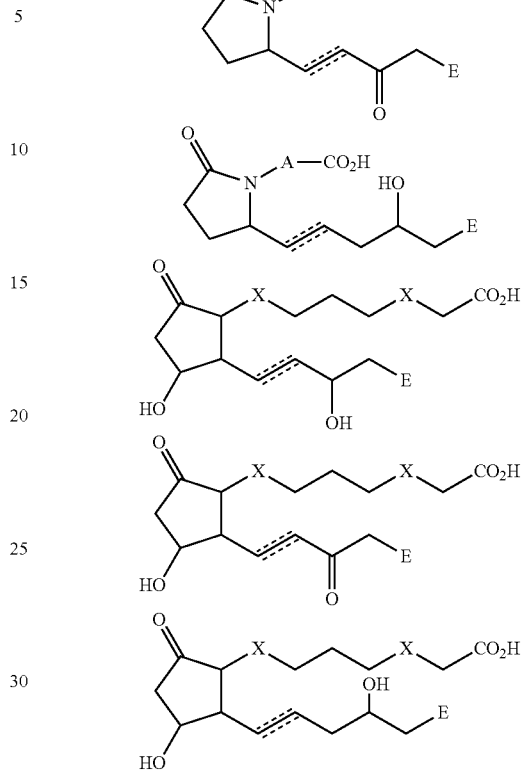

C$_{1-12}$ alkyl is alkyl having from 1 to 12 carbon atoms, including:

linear alkyl, such as methyl, ethyl, n-propyl, n-butyl, etc.;

branched alkyl, such as iso-propyl, iso-butyl, t-butyl, isopentyl, etc.;

cyclic alkyl, such as cyclopropyl, cyclobutyl, cyclohexyl, etc.; including substituted cycloalkyl, such as methylcyclohexyl, ethylcyclopropyl, dimethylcycloheptyl, etc, and including moieties such as CH$_2$-cyclohexyl, where the cyclic group is not the point of attachment to the rest of the molecule; and any combination of the other types of alkyl groups listed above. Thus, E may be any of these groups. In particular, E may be linear alkyl of C$_{1-6}$, especially butyl. Other particularly useful groups from which E may be selected include, without limitation, cyclohexyl, cyclopentyl, substituted cyclohexyl and cyclobutyl having less than 9 carbon atoms, and the like.

E may be R$^2$ or Y—R$^2$ wherein Y is CH$_2$, S or O and R$^2$ is aryl or heteroaryl. Thus, E may be aryl, heteroaryl, —CH$_2$-aryl, —S-aryl, —O-aryl, —CH$_2$-heteroaryl, —S-heteroaryl, —O-heteroaryl, and the like.

Aryl is defined as an aromatic ring or ring system as well as a substituted derivative thereof, wherein one or more substituents are substituted for hydrogen. While not intending to limit the scope of the invention in any way, phenyl, naphthyl, biphenyl, terphenyl, and the like are examples of aryl.

Heteroaryl is defined as aryl having at least one non-carbon atom in an aromatic ring or ring system. While not intending to limit the scope of the invention in any way, in many cases one or more oxygen, sulfur, and/or nitrogen atoms are present. While not intending to limit the scope of the invention in any way, examples of heteroaryl are furyl, thienyl, pyridinyl, benzofuryl, benzothienyl, indolyl, and the like.

The substituents of aryl or heteroaryl may have up to 12 non-hydrogen atoms each and as many hydrogens as necessary. Thus, while not intending to limit the scope of the invention in any way, the substituents may be:

hydrocarbyl, such as alkyl, alkenyl, alkynyl, and the like, and combinations thereof;

hydrocarbyloxy, meaning O-hydrocarbyl such as $OCH_3$, $OCH_2CH_3$, O-cyclohexyl, etc, up to 11 carbon atoms, and the like;

hydroxyhydrocarbyl, meaning hydrocarbyl-OH such as $CH_2OH$, $C(CH_3)_2OH$, etc, up to 11 carbon atoms, and the like;

nitrogen substituents such as $NO_2$, CN, and the like, including amino, such as $NH_2$, $NH(CH_2CH_3OH)$, $NHCH_3$, etc., up to 11 carbon atoms, and the like;

carbonyl substituents, such as $CO_2H$, ester, amide, and the like;

halogen, such as chloro, fluoro, bromo, and the like;

fluorocarbonyl, such as $CF_3$, $CF_2CF_3$, and the like;

phosphorous substituents, such as $PO_3^{2-}$, and the like;

sulfur substituents, including S-hydrocarbyl, SH, $SO_3H$, $SO_2$-hydrocarbyl, $SO_3$-hydrocarbyl, and the like.

In certain embodiments, the number of non-hydrogen atoms is 6 or less in a substituent. In certain embodiments, the number of non-hydrogen atoms is 3 or less in a substituent. In certain embodiments, the number of non-hydrogen atoms on a substituent is 1.

In certain embodiments, the substituents contain only hydrogen, carbon, oxygen, halo, nitrogen, and sulfur. The substituents may contain only hydrogen, carbon, oxygen, and halo.

In certain embodiments A is —$(CH_2)_6$—, cis —$CH_2CH=CH—(CH_2)_3$—, or —$CH_2C\equiv C—(CH_2)_3$—, wherein 1 or 2 carbon atoms may be substituted with S or O; and E is $C_{1-6}$ alkyl, $R^2$, or —Y—$R^2$ wherein Y is $CH_2$, S, or O, and $R^2$ is aryl or heteroaryl.

In one embodiment $R^1$ is H, chloro, or fluoro. In one embodiment $R^1$ is H. In one embodiment, $R^1$ is chloro.

$R^2$ may be phenyl, naphthyl, biphenyl, thienyl, or benzothienyl having from 0 to 2 substituents selected from the group consisting of F, Cl, Br, methyl, methoxy, and $CF_3$.

$R^2$ may be $CH_2$-naphthyl, $CH_2$-biphenyl, $CH_2$-(2-thienyl), $CH_2$-(3-thienyl), naphthyl, biphenyl, 2-thienyl, 3-thienyl, $CH_2$-(2-(3-chlorobenzothienyl)), $CH_2$-(3-benzothienyl), 2-(3-chlorobenzothienyl), or 3-benzothienyl.

$R^2$ may be $CH_2$-(2-thienyl), $CH_2$-(3-thienyl), 2-thienyl, 3-thienyl, $CH_2$-(2-(3-chlorobenzothienyl)), $CH_2$-(3-benzothienyl), 2-(3-chlorobenzothienyl), or 3-benzothienyl.

While not intending to limit the scope of the invention in any way, compounds according to the structures below, wherein x is 0 or 1 and $R^1$ is H, chloro, fluoro, bromo, methyl, methoxy, or $CF_3$, are examples of prostaglandin $EP_4$ agonists.

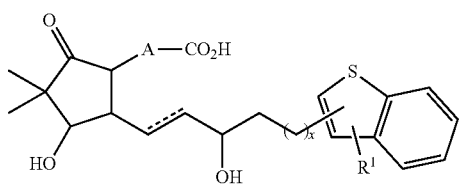

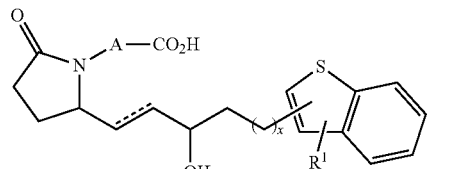

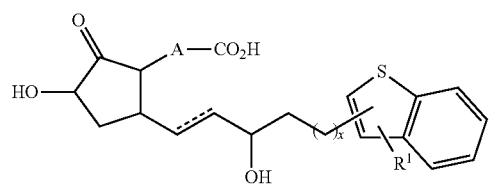

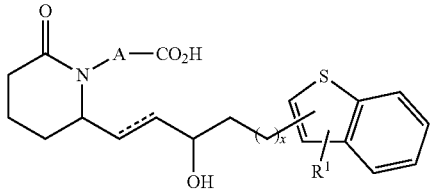

While not intending to limit the scope of the invention in any way, compounds according to the structures below are examples of prostaglandin $EP_4$ agonists.

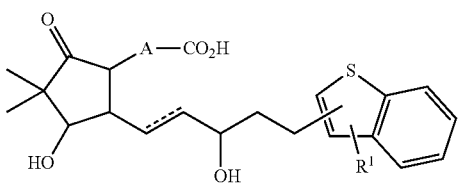

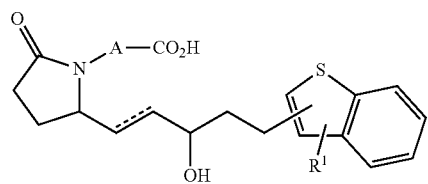

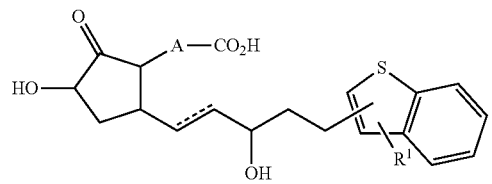

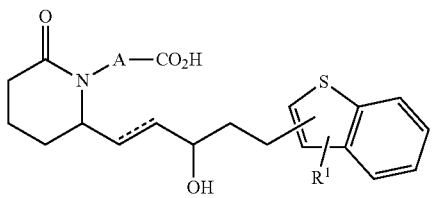

While not intending to limit the scope of the invention in any way, compounds according to the structures below are examples of prostaglandin $EP_4$ agonists.

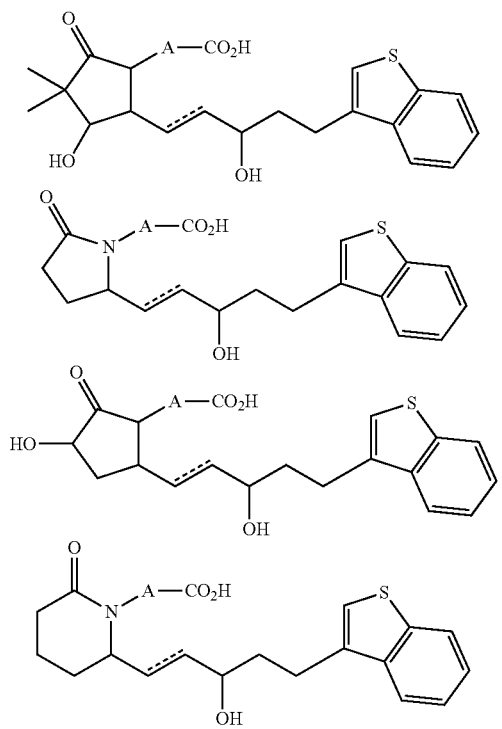

While not intending to limit the scope of the invention in any way, compounds according to the structures below are examples of prostaglandin EP$_4$ agonists.

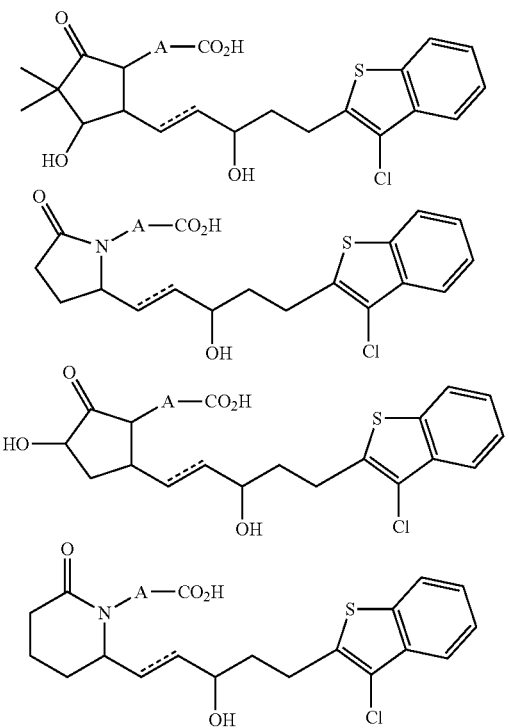

While not intending to limit the scope of the invention in any way, compounds according to the structures below, wherein x is 0 or 1 and R$^1$ is H, chloro, fluoro, bromo, methyl, methoxy, or CF$_3$, are examples of prostaglandin EP$_4$ agonists.

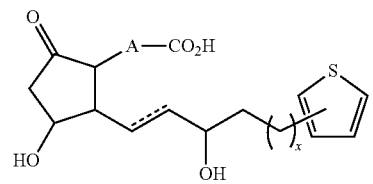
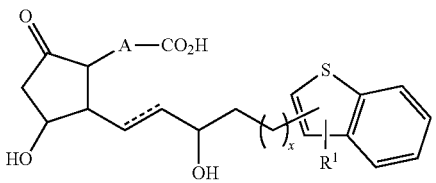
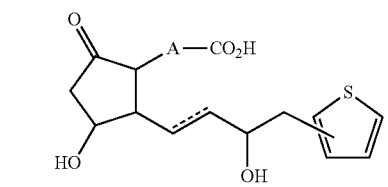
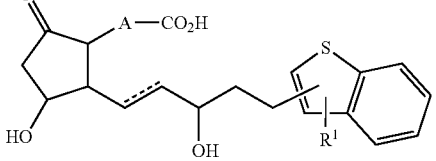
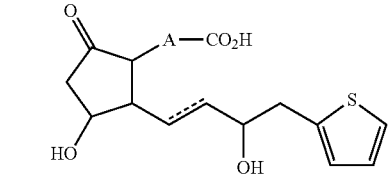
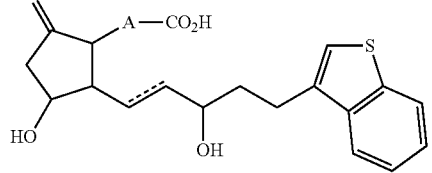
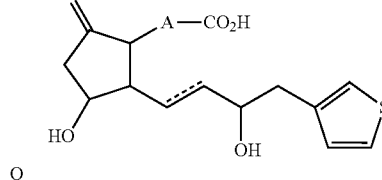
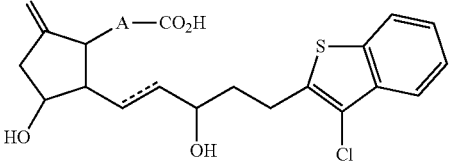

While not intending to limit the scope of the invention in any way, compounds according to the structures below are examples of prostaglandin EP$_4$ agonists.

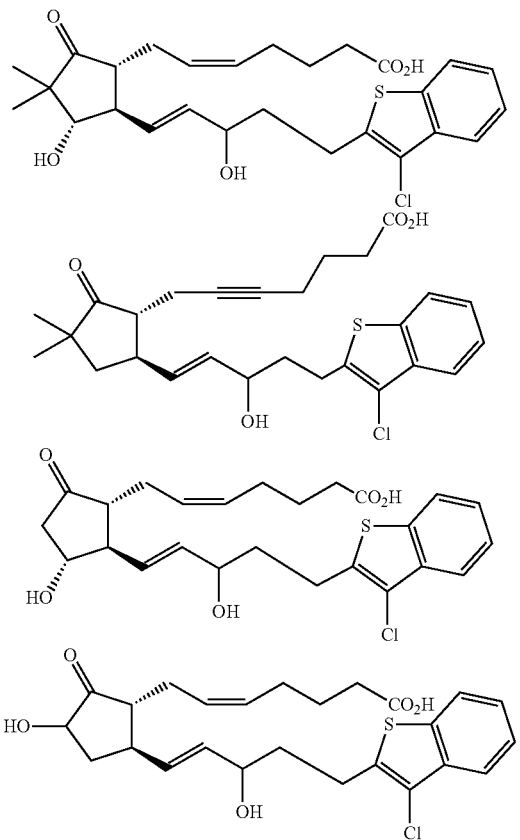

Furthermore, the following United States Patent Applications or Patents, all of which are expressly incorporated by reference herein, disclose compounds which are prostaglandin $EP_4$ agonists: U.S. Pat. No. 6,552,067; U.S. Pat. No. 6,747,054; United States Patent Application Publication No. 20030120079; United States Patent Application Publication No. 20030207925; United States Patent Application Publication No. 20040157901; U.S. Pat. No. 4,117,014; U.S. Patent Application Publication No. 2004/0142969; U.S. Pat. Nos. 6,747,037; 6,610,719; 4,171,375; 3,931,297; U.S. patent application Ser. No. 821,705, filed Apr. 9, 2004; U.S. Pat. Nos. 6,670,485; 6,410,591; and 6,538,018.

All prostaglandin $EP_4$ agonists, pharmaceutically acceptable salts of all prostaglandin $EP_4$ agonists and prodrugs related to all prostaglandin $EP_4$ agonists are contemplated herein as prostagiandin $EP_4$ agonist components.

Prodrugs of prostaglandin $EP_4$ agonists comprising

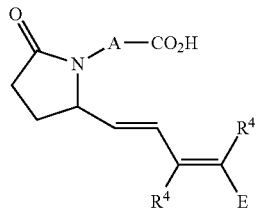

are contemplated herein;

wherein $R^4$ is H, halo or $C_{1-6}$ alkyl.

Halo is a group 7 atom such as fluoro, chloro, bromo, iodo, and the like.

$C_{1-6}$ alkyl is a linear, branched, or cyclic alkyl having from 1 to 6 carbons including, but not limited to, methyl, ethyl, propyl, butyl, pentyl, hexyl, cyclopropyl, cylobutyl, cyclohexyl, and the like.

While not intending to limit the scope of the invention in any way, prodrugs of prostaglandin $EP_4$ agonists according to the structures below are contemplated.

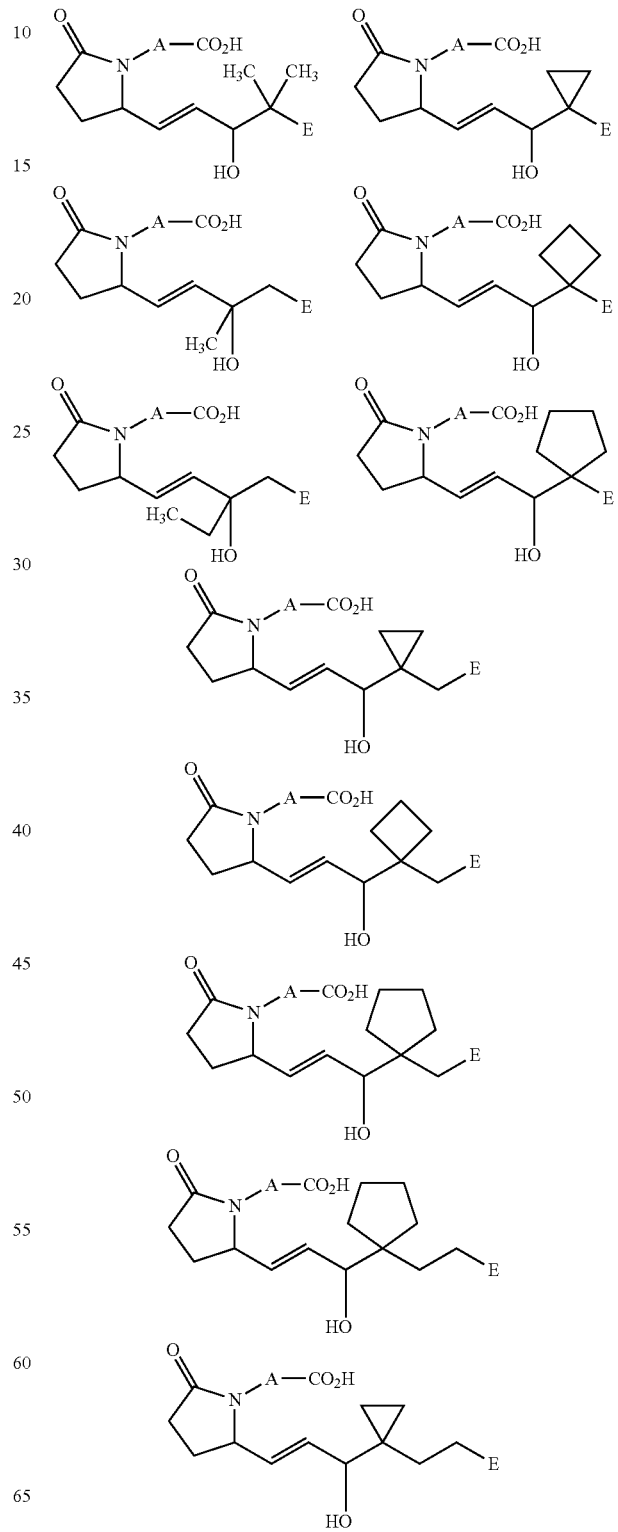

-continued

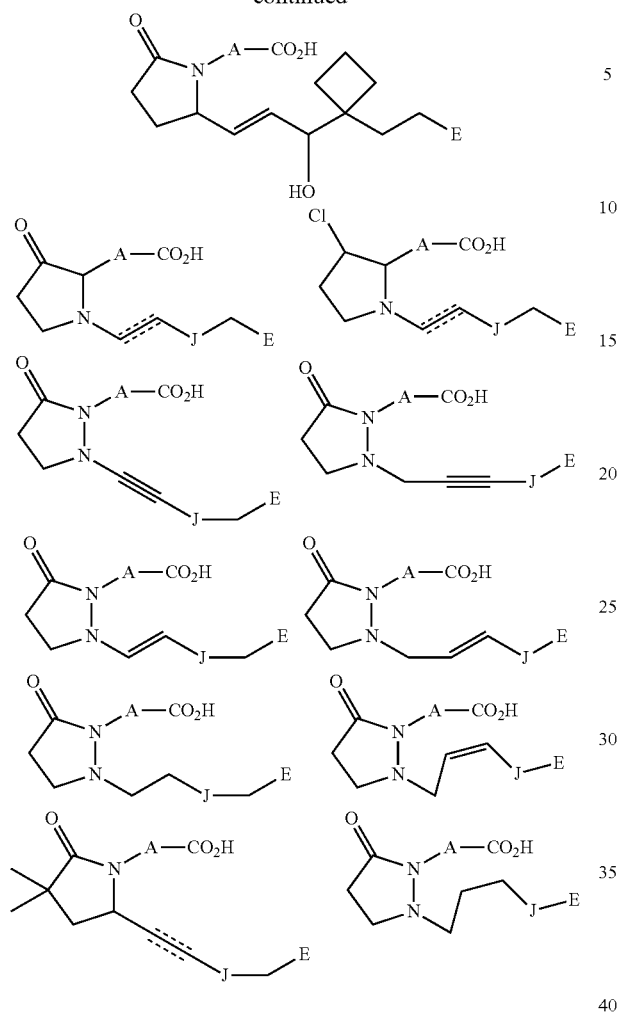
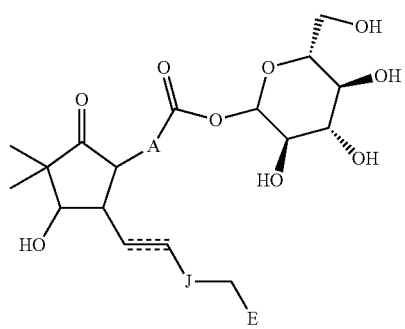
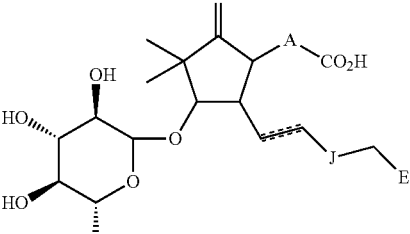
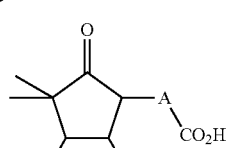
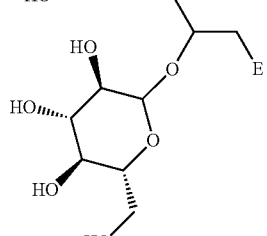
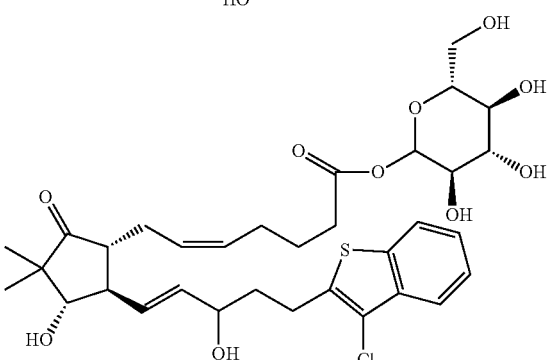
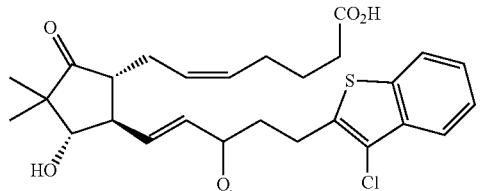
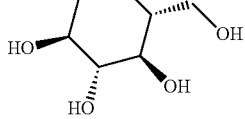

The term carbohydrate is defined broadly to encompass simple sugars, disaccharides, oligosaccharides, polysaccharides, starches, and the like, whether linear, branched or macrocyclic. The term carbohydrate also refers to one of the foregoing classes of compounds having up to one amine functional group present for every six carbon atoms.

The esters, ethers, or amide prodrugs herein may incorporate either a direct bond to the carbohydrate or amino acid, or may alternatively incorporate a spacer group including, but not limited to, polyols such as ethylene glycol, glycerine, and the like, and oligomers and polymers thereof;

dicarboxylic acids, such as succinic acid, maleic acid, malonic acid, azelaic acid, and the like;

hydroxycarboxylic, acids such as lactic acid, hydroxyacetic acid, citric acid, and the like;

polyamines, such as ethylene diamine and the like; and esters, amides, or ethers to form combinations of any of the above.

In certain embodiments, the prodrug is a glucoside ester or ether. Thus, without limiting the scope of the invention in any way, compounds like those shown below, or pharmaceutically acceptable salts thereof, are useful as prostaglandin $EP_4$ agonist components in accordance with the present invention.

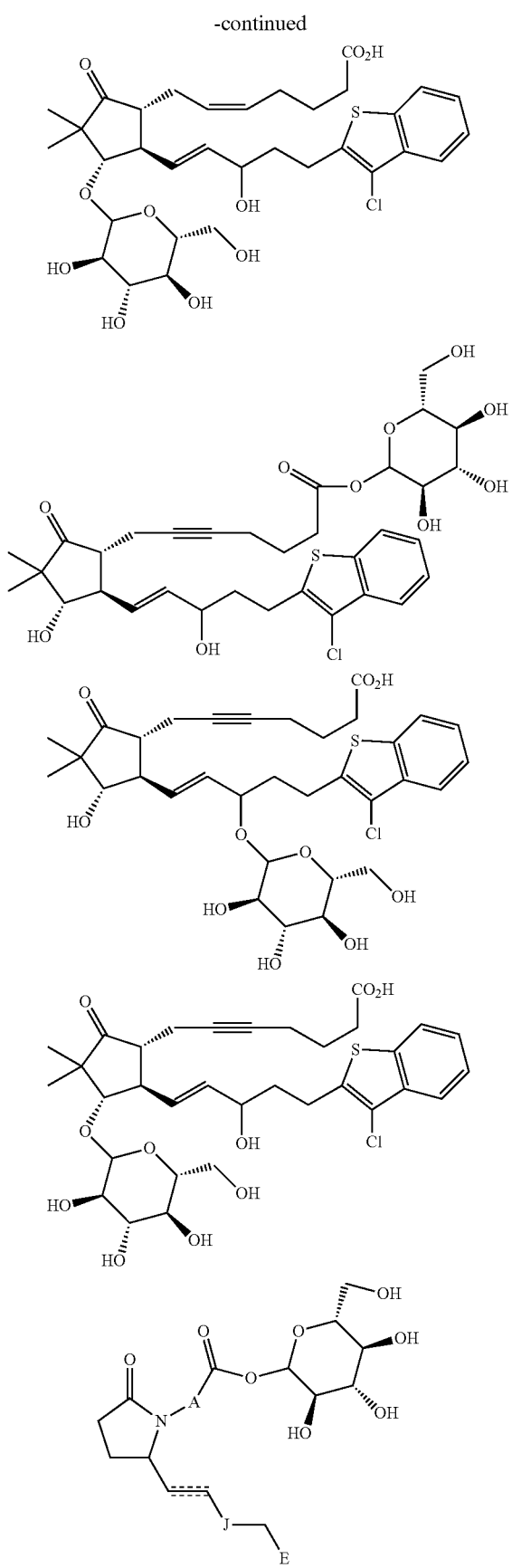
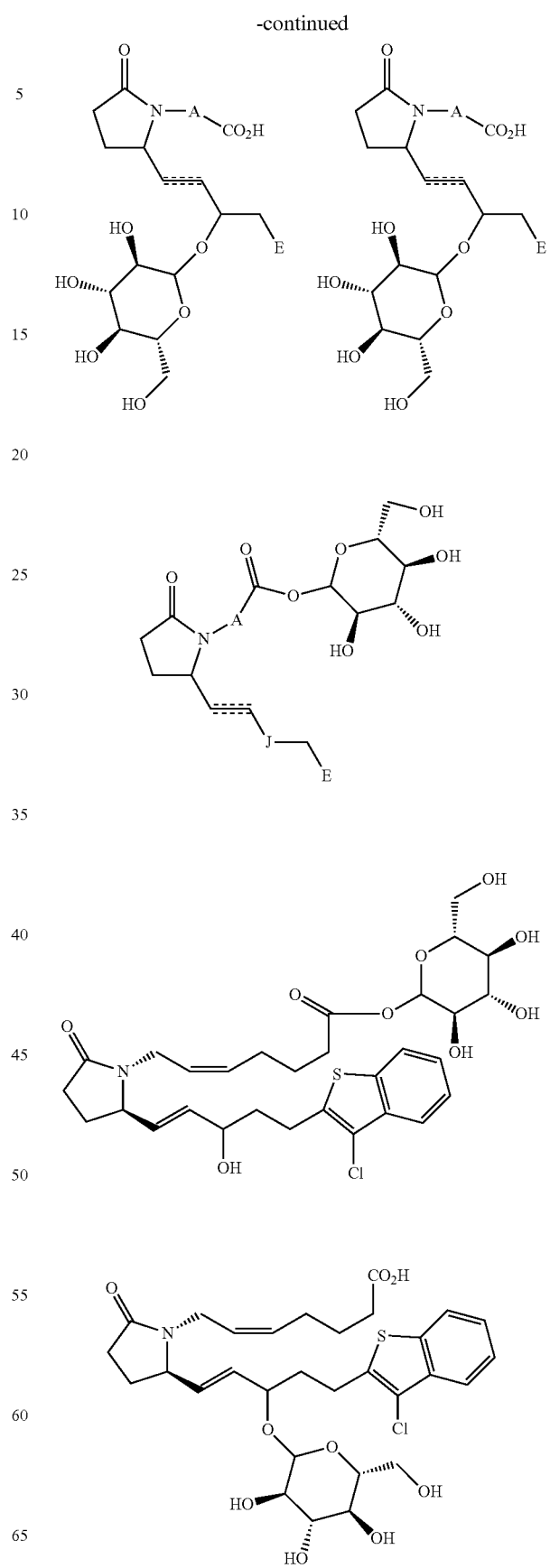

-continued
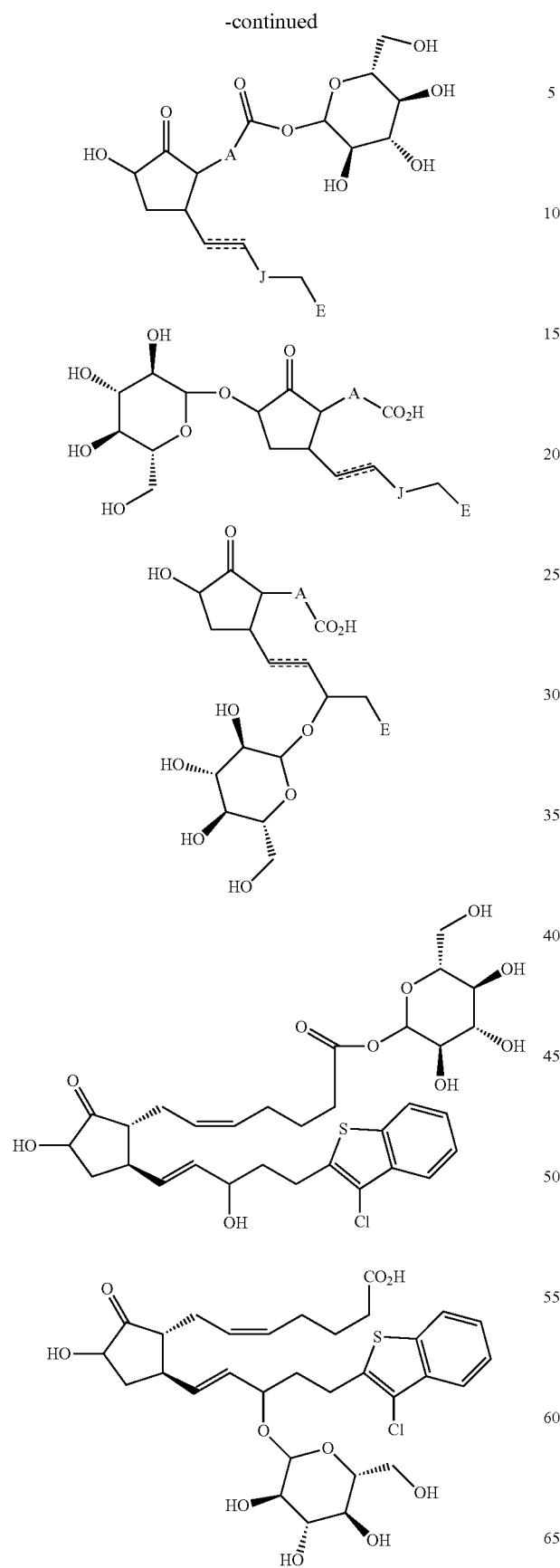
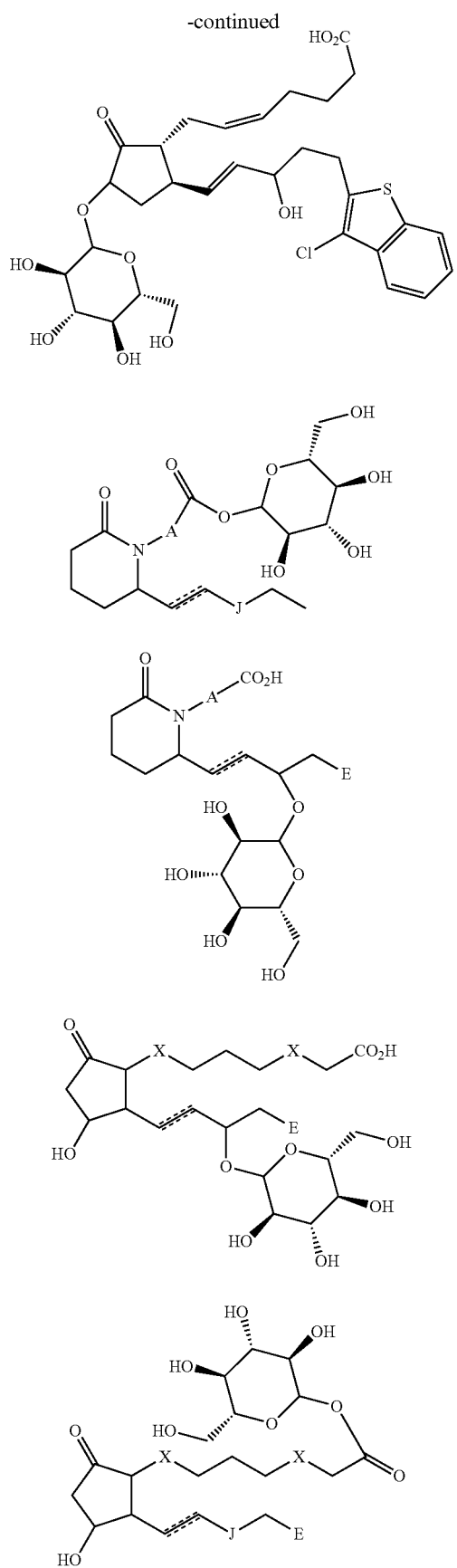

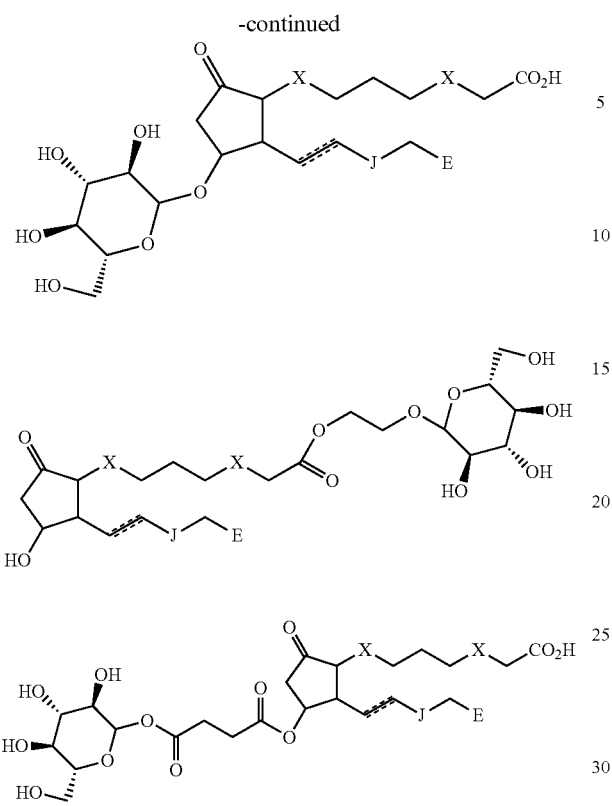

Alternatively, the ester or ether bond may occur at a different position on the sugar; i.e. the oxygen of one of the other hydroxyl groups is the oxygen of the ester or ether bond.

In one embodiment, the prodrug is a glucuronide ester or ether. Thus, without limiting the scope of the invention in any way, compounds like those shown below, or pharmaceutically acceptable salts thereof, are useful as prostaglandin $EP_4$ agonist components in accordance with the present invention.

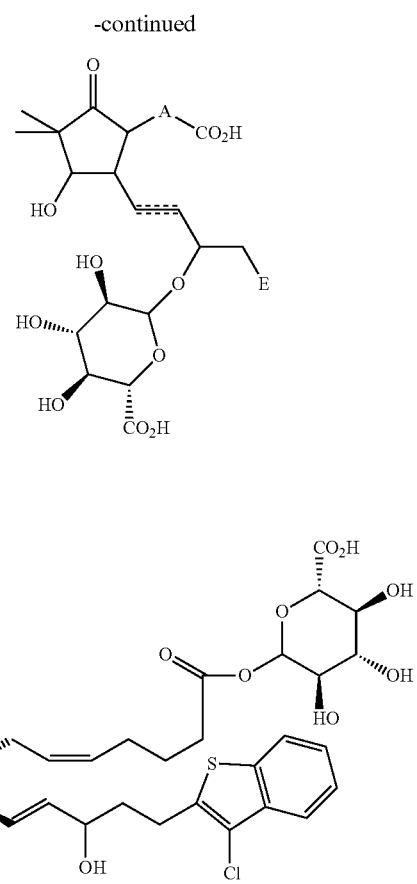

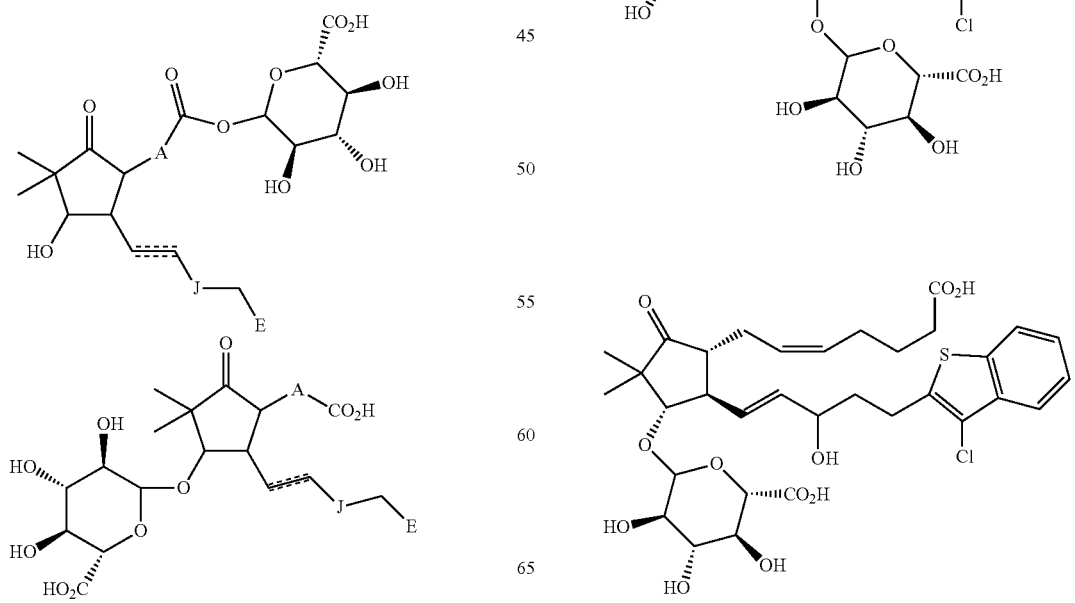

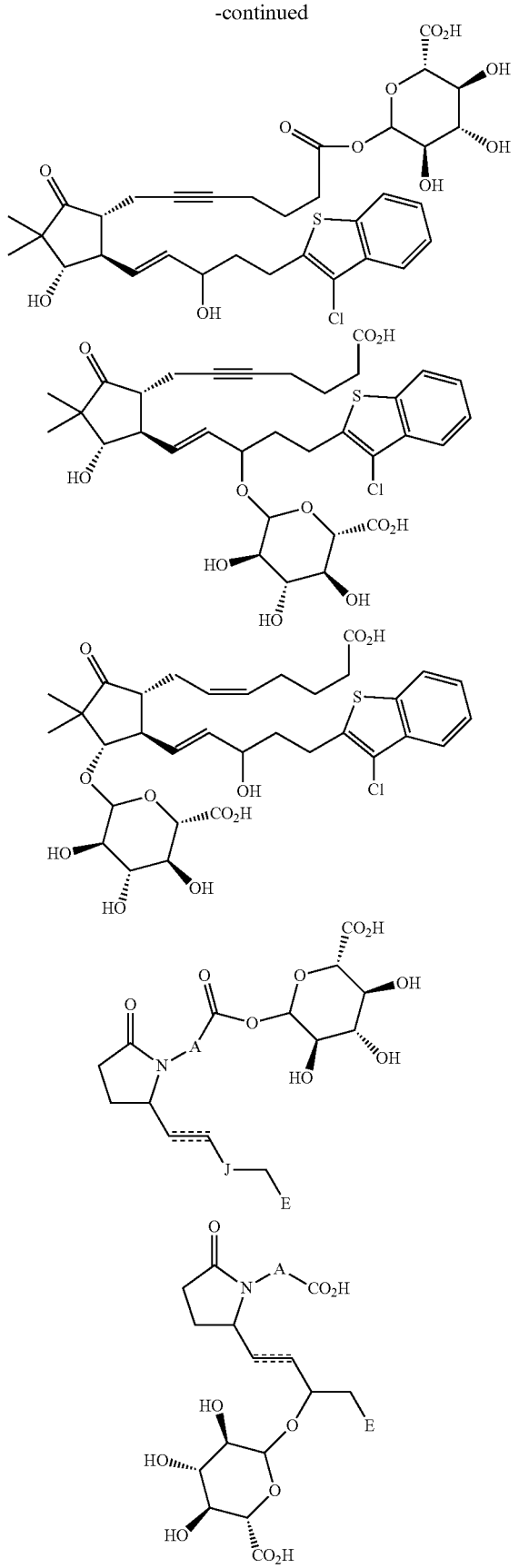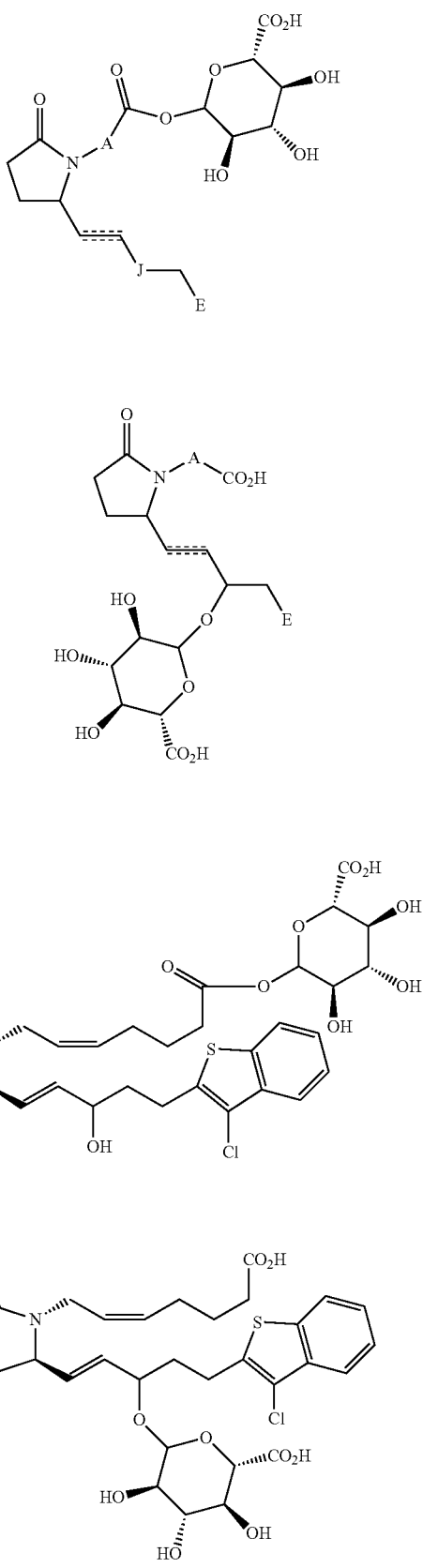

-continued
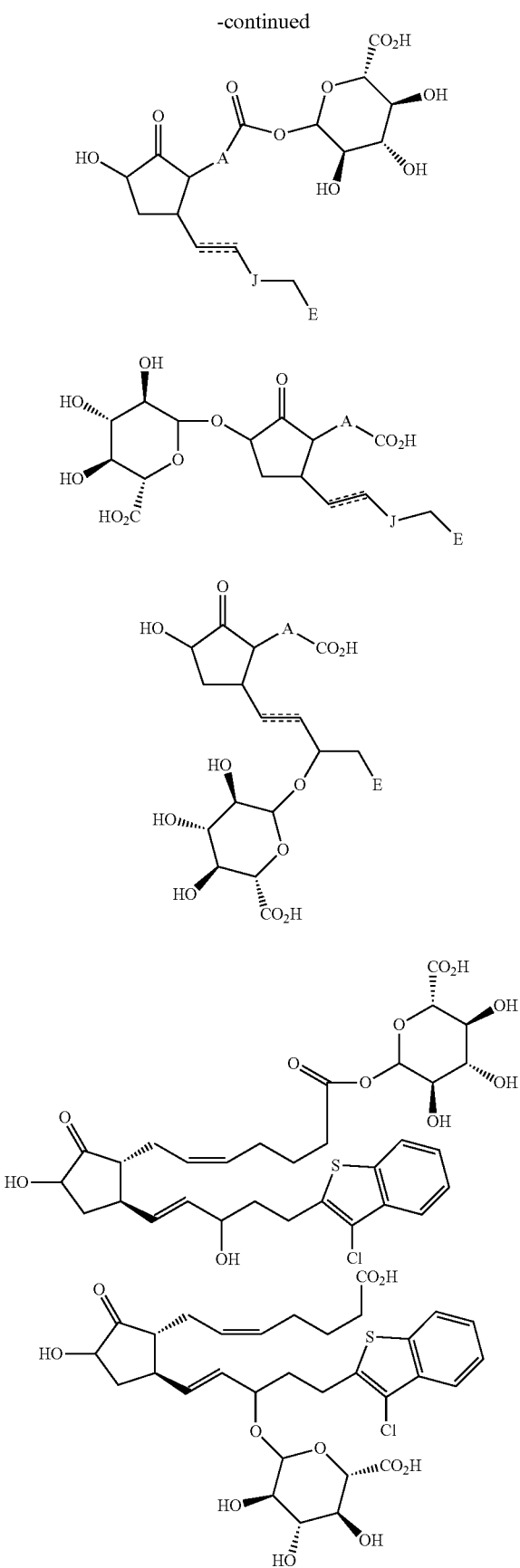
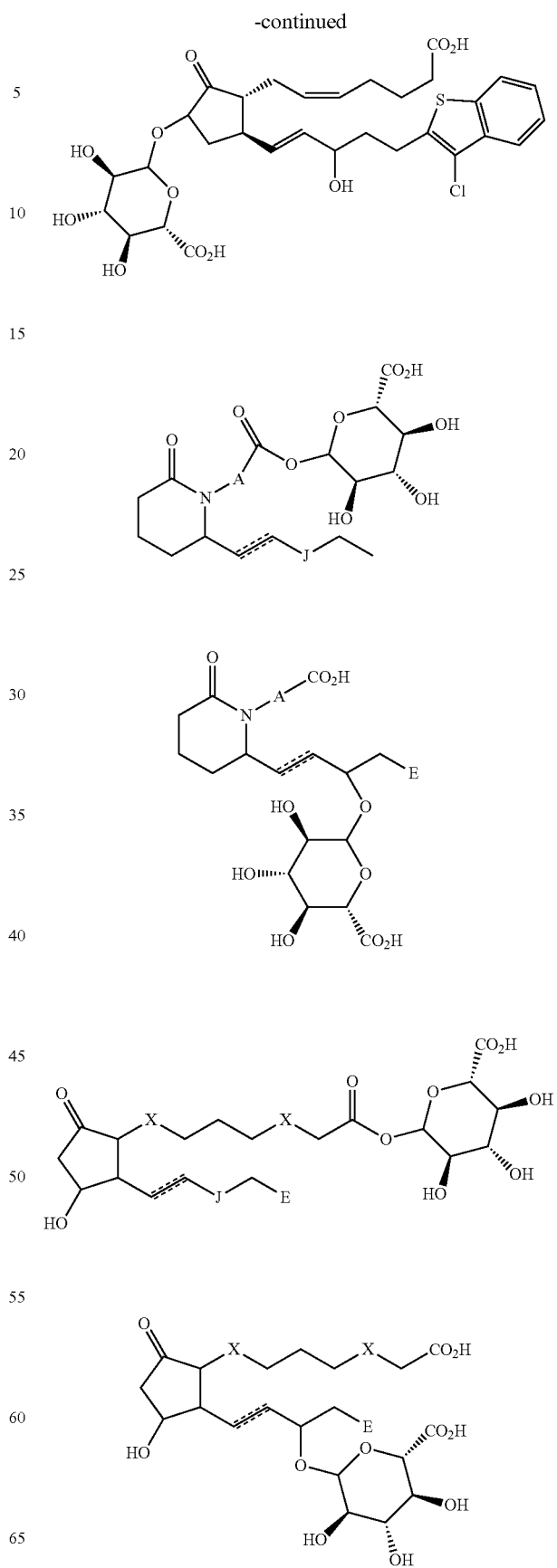

-continued

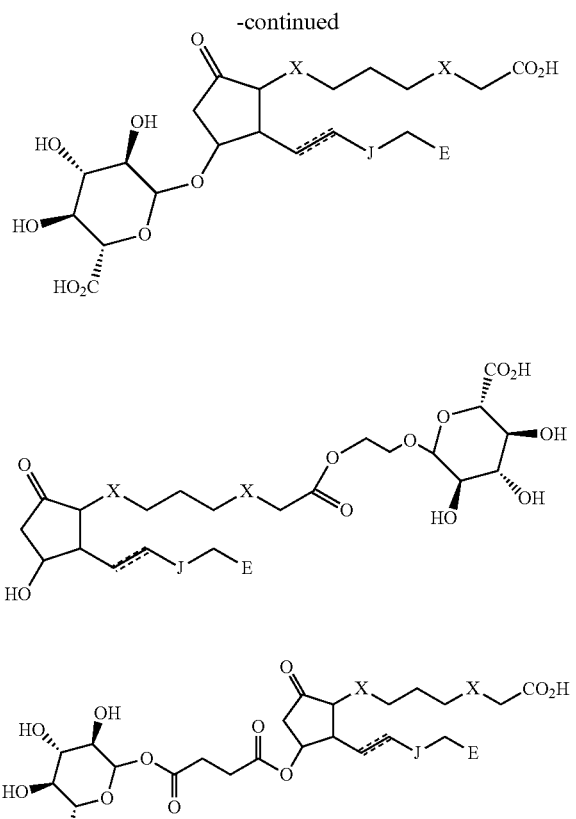

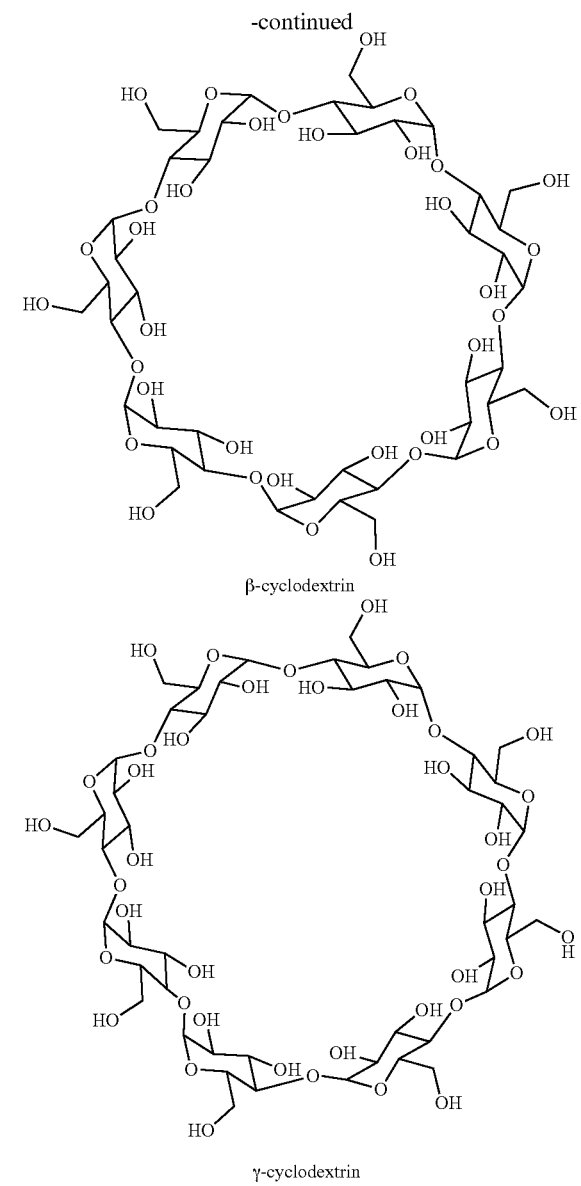

β-cyclodextrin

γ-cyclodextrin

Alternatively, the ester or ether bond may occur at a different position on the sugar; i.e. the oxygen of one of the other hydroxyl groups is the oxygen of the ester or ether bond.

Other prodrugs are cyclodextrin esters. Cyclodextrins are cyclic oligosaccharides containing 6, 7, or 8 glucopyranose units, referred to as α-cyclodextrin, β-cyclodextrin, or γ-cyclodextrin respectively (structures depicted below).

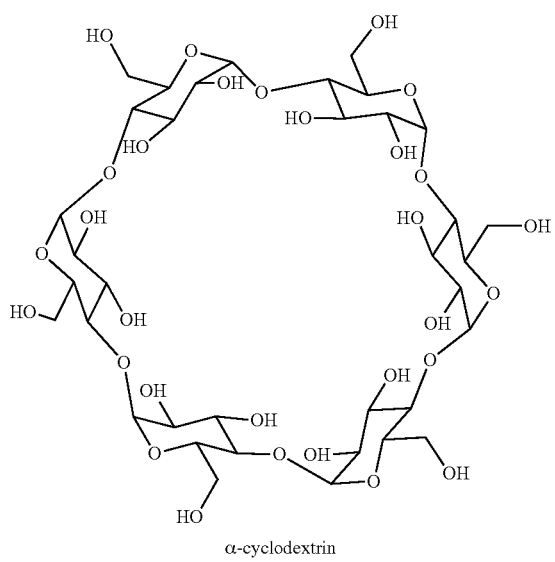

α-cyclodextrin

Thus, without limiting the scope of the invention in any way, compounds like those shown below, or pharmaceutically acceptable salts thereof, are useful as prostaglandin $EP_4$ agonist components in accordance with the present invention.

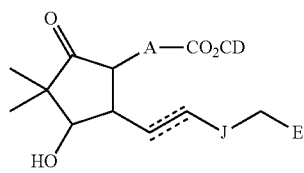

In any structure disclosed herein, CD indicates a cyclodextrin or a spacer-cyclodextrin, including α-, β-, and γ-cyclodextrin, which may be attached at a 2-, 3-, or 6-hydroxyl group. A 2-, 3-, or 6-hydroxyl group refers to the position on the glucose monomer where the anomeric carbon is 1 and the terminal carbon (in the chain form) is 6. The following examples illustrate this nomenclature.

For the compound below, CD is α-cyclodextrin linked at a 3-hydroxyl group.
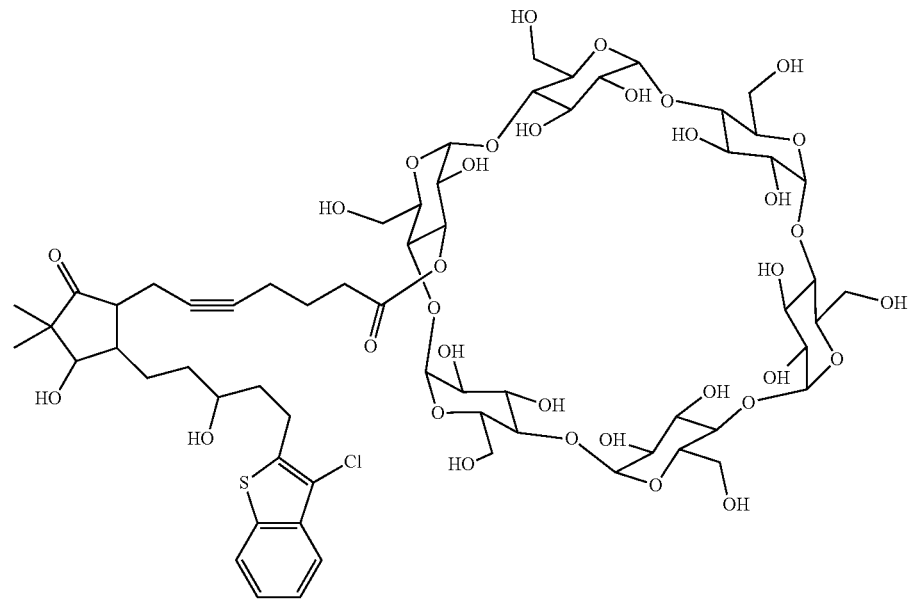
For the compound below, CD is an ethylene glycol-β-cyclodextrin linked at a 2-hydroxyl group.
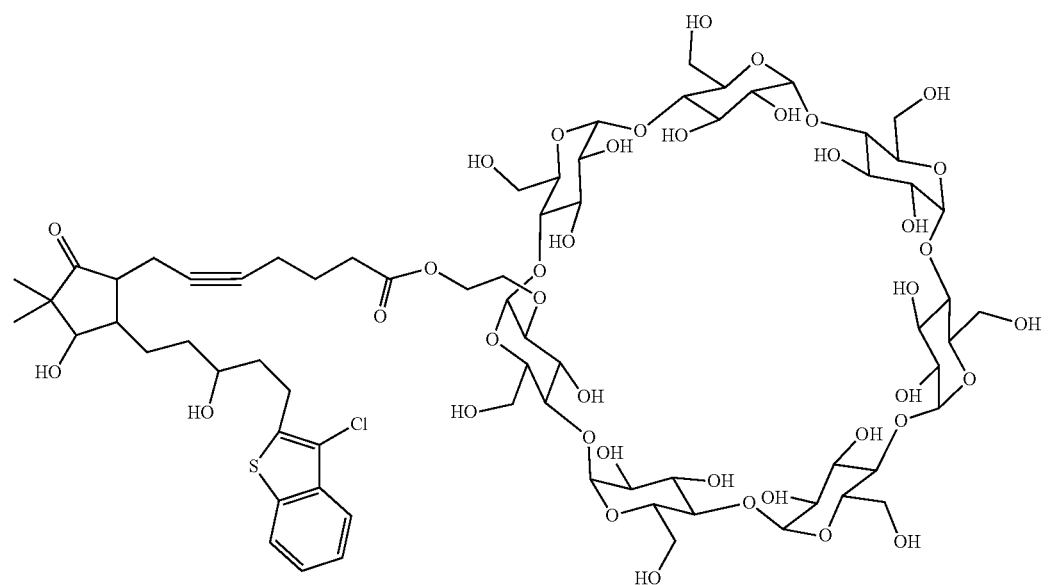

For the compound below, CD is a γ-cyclodextrin linked at a 6-hydroxyl group.

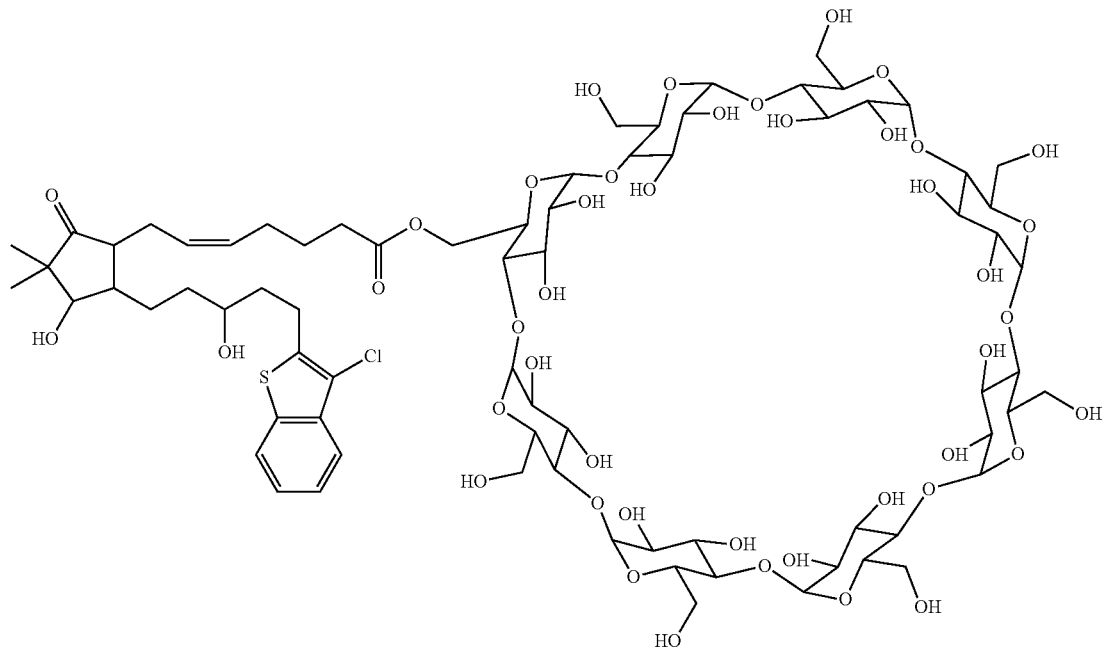

The CD esters shown below, as well as pharmaceutically acceptable salts thereof, are also useful prostaglandin $EP_4$ agonist prodrug compounds.

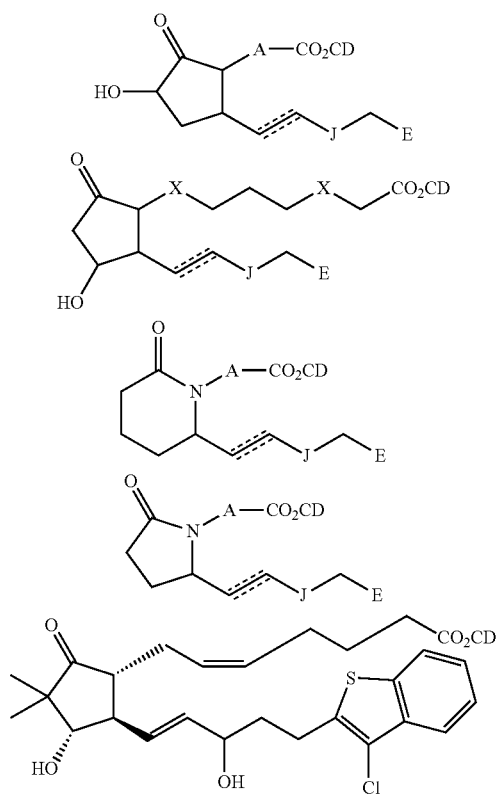

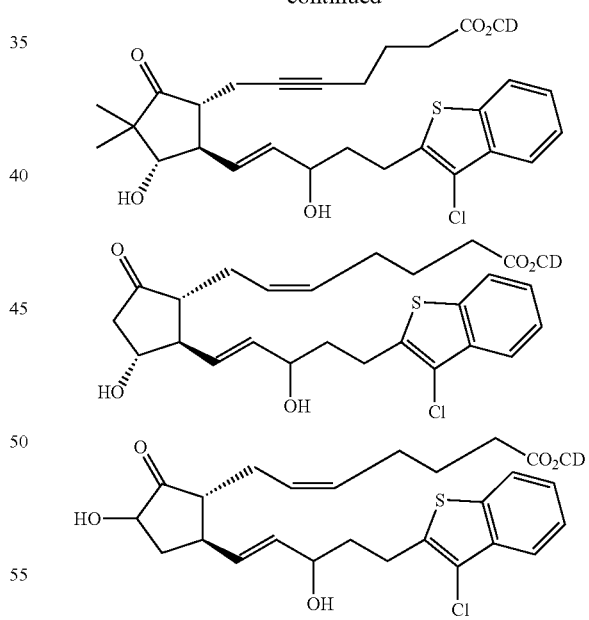

Dextran esters are also useful prodrugs. Dextran is a polymer of glucose primarily linked of α-D(1→6), i.e. D-glucose units are linked by a bond between an α-hydroxyl group at the anomeric (position 1) carbon and the hydroxyl group at carbon 6.

The dextran esters shown below are especially useful as prodrugs, as well as their pharmaceutically acceptable salts. Dx is dextran or spacer-dextran, where the O in $CO_2$ comes from a dextran hydroxyl group or from a spacer bonded to a dextran hydroxyl group, analogous to the structures shown for cyclodextrin esters.

amide nitrogen may be connected as per proline. Pharmaceutically acceptable salts of compounds of these structures, whether anionic, cationic, or zwitterionic, are also useful.

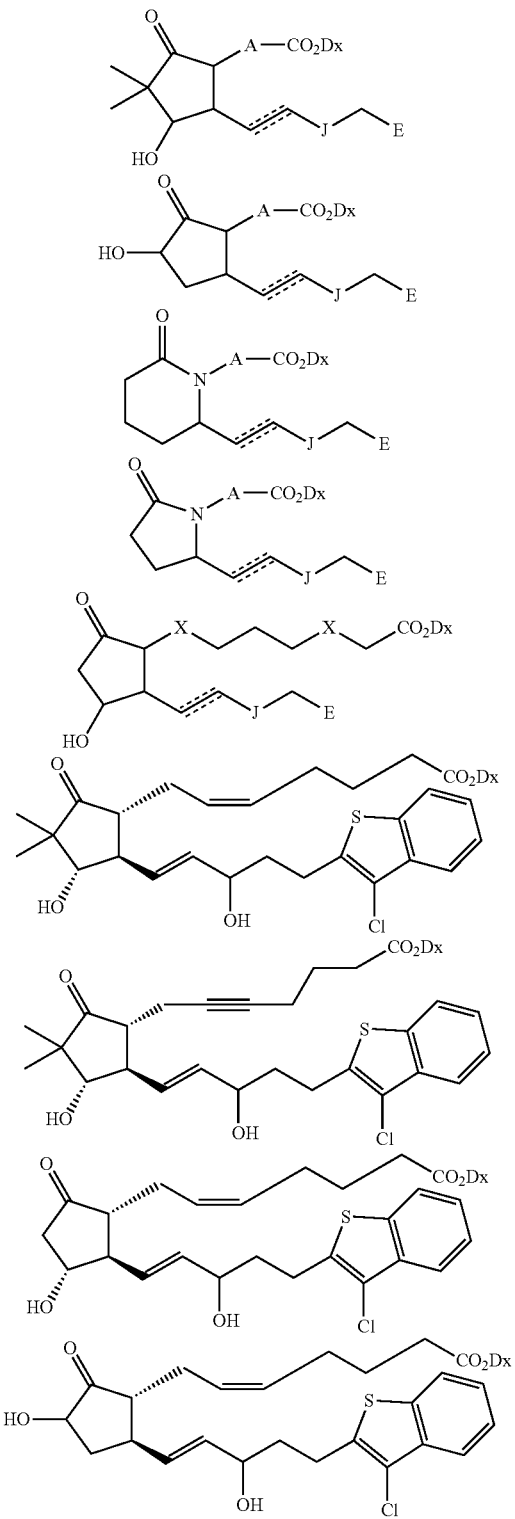

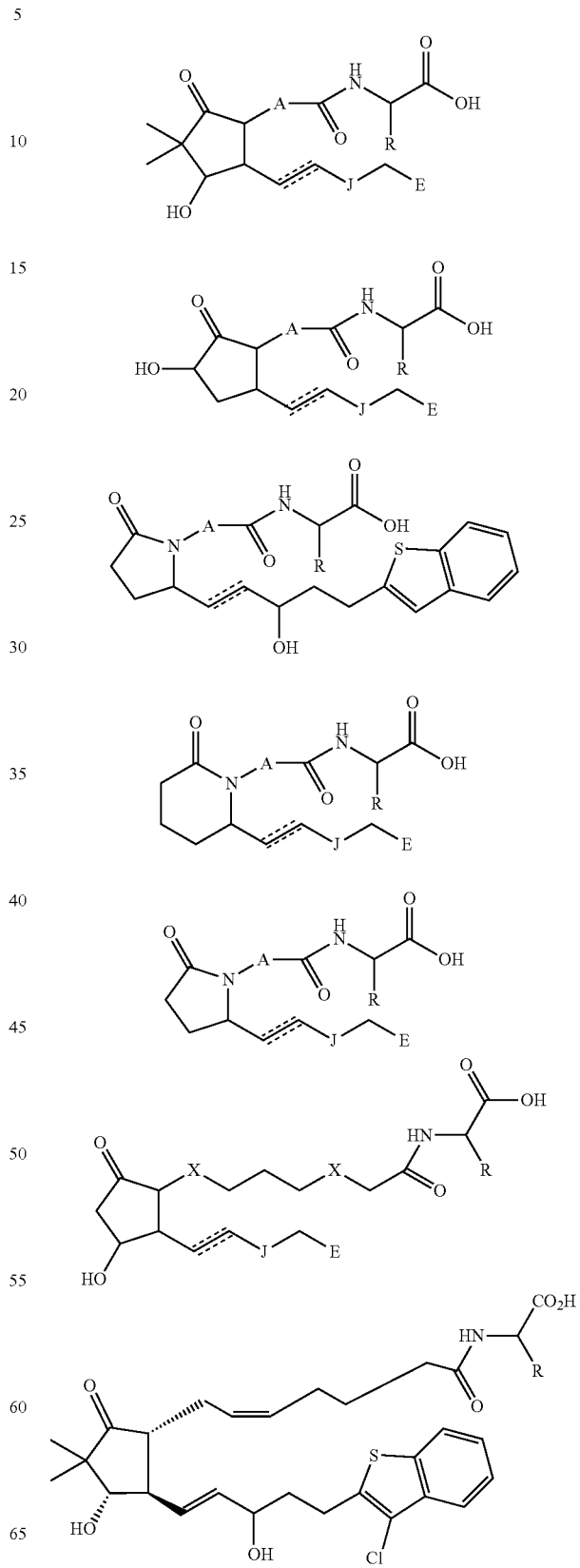

Amino acid prodrugs are also contemplated, such as in the structures shown below, where R represents the side chain characteristic of a natural amino acid, and where R and the

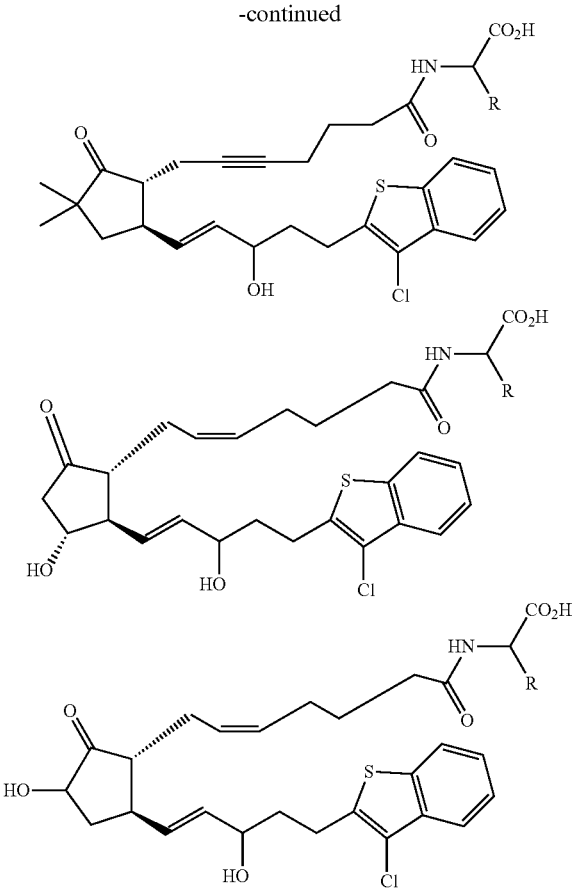

In certain embodiments, R is selected from the group consisting of H, methyl, iso-propyl, sec-butyl, benzyl, indol-3-ylmethyl, hydroxymethyl, $CHOHCH_3$, $CH_2CONH_2$, p-hydroxybenzyl, $CH_2SH$, $(CH_2)_4NH_2$, $(CH_2)_3NHC(NH_2)_2^+$, methylimidizol-5-yl, $CH_2CO_2H$, $(CH_2)_2CO_2H$ and the like.

Ester prodrugs of $EP_4$ agonists may also be based upon amino acids, as demonstrated by the examples shown below. Pharmaceutically acceptable salts of compounds of these structures, whether anionic, cationic, or zwitterionic, are also useful.

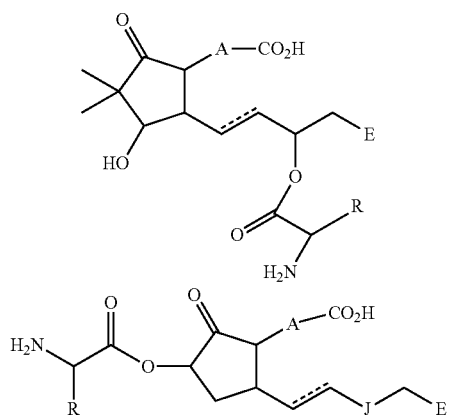

Since amino acids such as serine, threonine, and tyrosine have hydroxyl functional groups in their side chains, ether prodrugs of $EP_4$ agonists based upon amino acids are also possible, as demonstrated in the examples below. Pharmaceutically acceptable salts of compounds of these structures, whether anionic, cationic, or zwitterionic, are also useful.

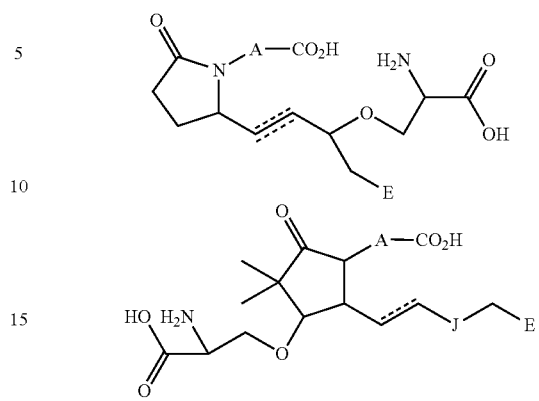

In addition, the spacers illustrated herein may be applied to amino acids to further increase the number and kinds of useful amino acid prodrugs.

Since a carbohydrate according to the definition given herein may have a limited amount of amine functional groups, carbohydrate amides are also possible such as the ones depicted below.

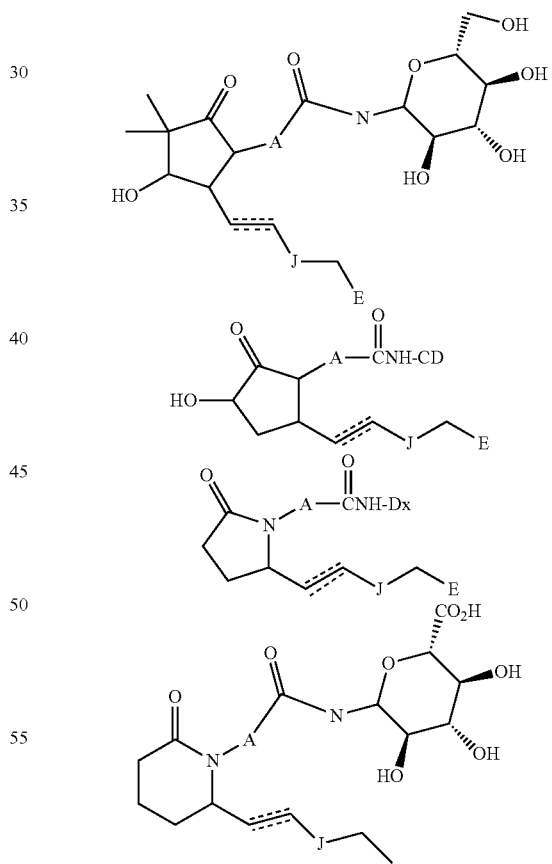

Analogous structures could also be drawn with any of the carbohydrate esters shown herein, making a large variety of carbohydrate amides possible for use in the methods disclosed herein. Further, since the prodrugs may incorporate an amine spacer, the number of carbohydrate amides contemplated is further diversified.

Prodrugs of the compounds shown below, and use of the compounds, or salts or prodrugs thereof, for any method, composition, or treatment disclosed herein, are specifically contemplated herein.

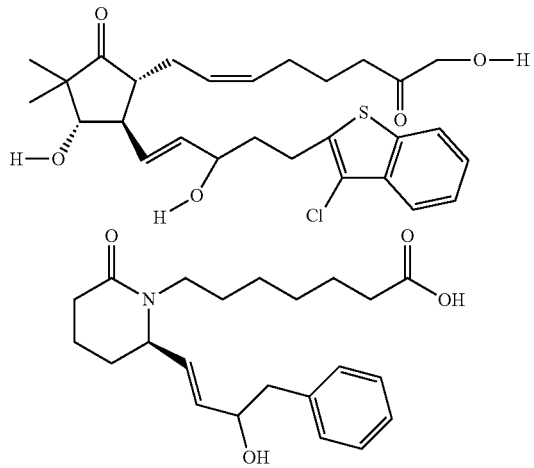

Unless indicated by a wedge or a dash, a carbon which has a chiral center can be construed to include the S isomer, the R isomer, or any mixture of isomers including a 50:50 R/S mixture. In particular, the pure isomers of each of the structures above, and any possible isomeric mixtures, including the 50:50 R/S mixtures, are contemplated. Methods of preparing these compounds are in U.S. Pat. Nos. 6,747,037 and 6,875,787, the disclosure of which are hereby incorporated in their entireties herein by reference.

There are a number of methods of preparing the prodrug compounds disclosed herein. While not intending to limit the scope of the invention in any way, a glucoside ether of a prostaglandin $EP_4$ agonist may be prepared from commercially available (Sigma Chemical Co.) 2,3,4,6-tetra-O-acetyl-β-D-glucopyranoside (2) by coupling the two in $CCl_4$ in the presence of silver carbonate, followed by hydrolysis of the ester protecting groups using a procedure adapted from Friend and Chang (*J. Med. Chem.* 1984, 27, 261-266; *J. Med. Chem.* 1985, 28, 51-57).

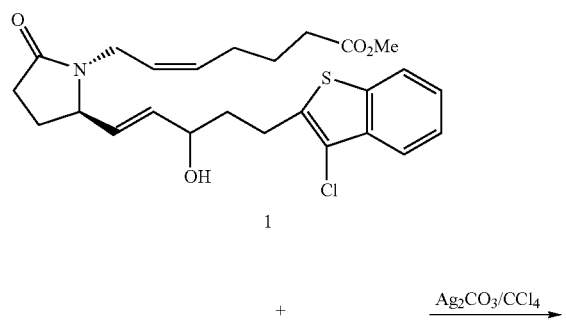

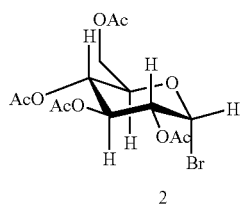

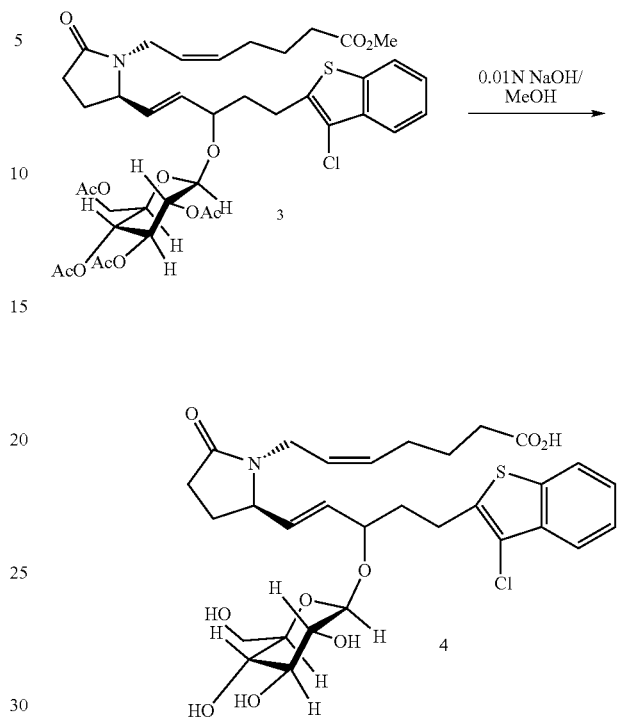

In this method, compound 1 is dissolved in dry $CCl_4$ or another suitable solvent, and freshly prepared $Ag_2CO_3$ (about 4.5 equivalents) is added. Compound 2 (about 2.7 equivalents) is then added dropwise while protecting the reaction mixture from light, and continuously distilling the solvent. The distilled solvent is replaced with fresh solvent during the course of the reaction. When the reaction is complete, the solution is worked up according to standard methods and purified by flash chromatography on RP-18 or another suitable purification method to yield compound 3. The ester groups of compound 3 are then saponified according to an art acceptable procedure such as NaOH in MeOH, and worked up and purified according to standard procedures.

This procedure may be used for prostaglandin $EP_4$ agonists having a single hydroxyl group. Alternatively, prodrugs for prostaglandin $EP_4$ agonists having more than 1 hydroxyl group may be prepared by protection of the hydroxyl groups with different groups, so that one may be removed for preparation of a prodrug. Generally, the ring, the α-chain, and the ω-chain are prepared separately and coupled toward the end of the synthetic procedure, so protection with distinct groups for each part is within the ability of a person of ordinary skill in the art.

A similar procedure may be used to prepare glucouronide ethers. Haeberlin et. al. (*Pharmaceutical Research* 1993, 10, 1553-1562) discloses such a procedure which may be adapted here.

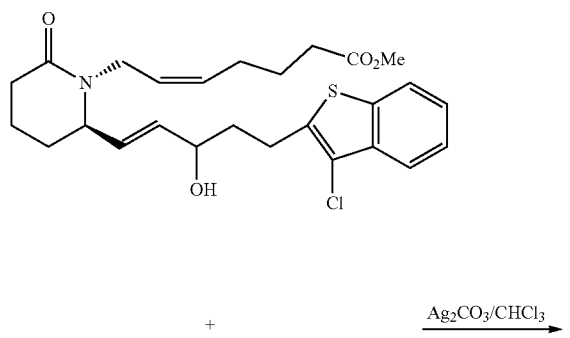

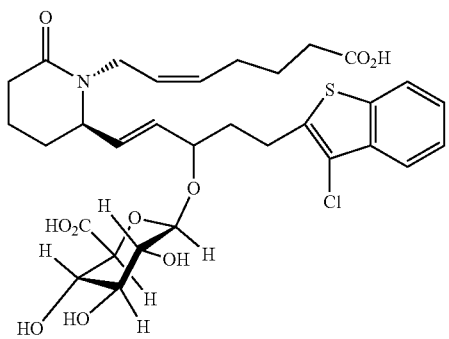

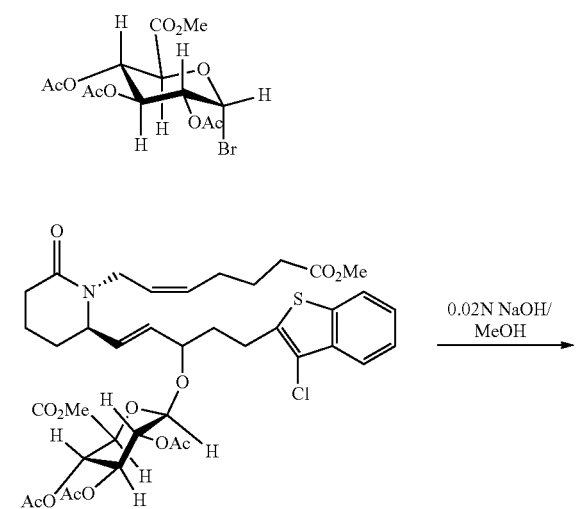

The procedure shown below may be used to link prostaglandin $EP_4$ agonists to cyclodextrin or to another carbohydrate. Coupling of the succinic acid to cyclodextrin is carried out as described by Tanaka et. al. (*Journal of Antibiotics* 1994, 47, 1025-1029), by suspending cyclodextrin in DMF, dissolving the mixture in pyridine, adding 1.2 equivalents of succinic anhydride, and stirring for 18 hours at room temperature. The mixture is poured into chloroform to precipitate the succinate ester product, which is filtered, washed with chloroform and methanol, and purified by an ODS column. Tanaka showed that reaction occurs preferentially at the 6 OH by a ratio of 4.6/1 for succinic anhydride. The preference reaction at the 6-OH is even greater for phthalic anhydride (13.6/1), naphthalene dicarboxylic anhydride (14.0/1), and cyclohexane dicarboxylic anhydride (14.7/1).

The hydroxyl group of the prostaglandin $EP_4$ agonist is activated by reacting with p-toluenesulfonyl chloride, and the tosylate 7 is reacted with the cyclodextrin derivative 6 to obtain the prodrug product.

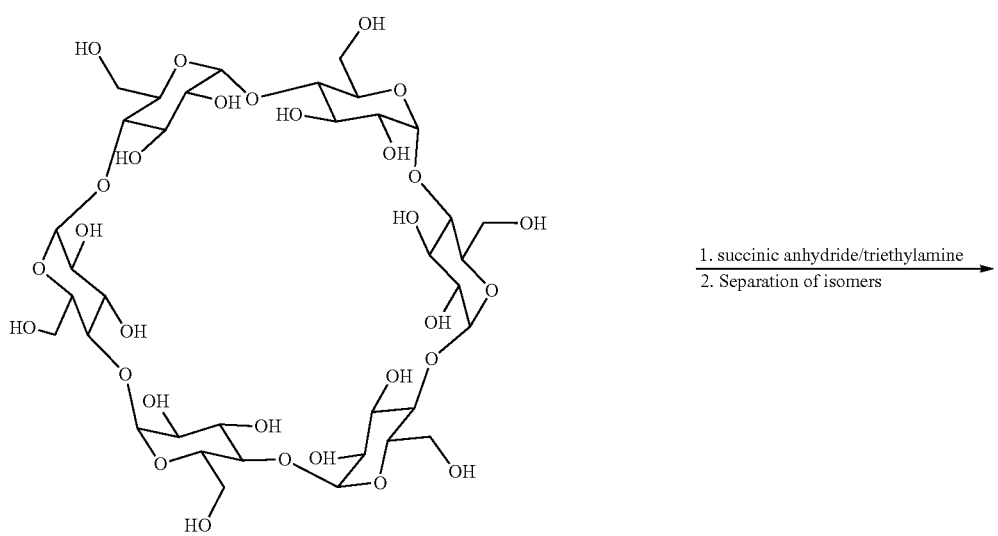

-continued

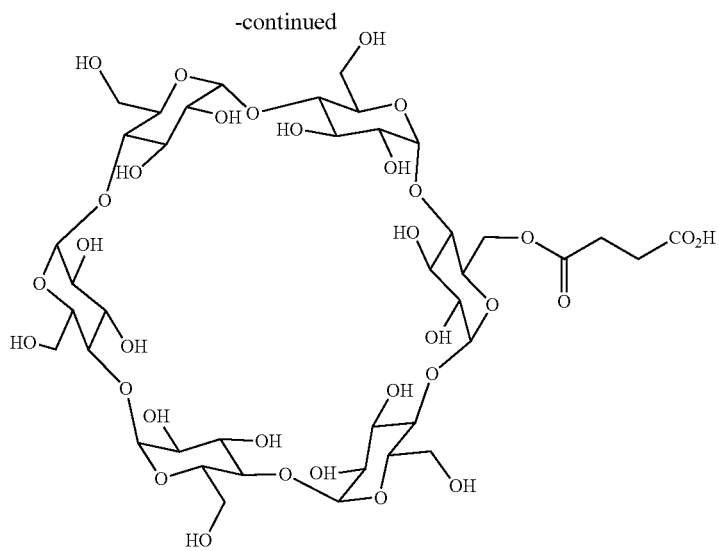

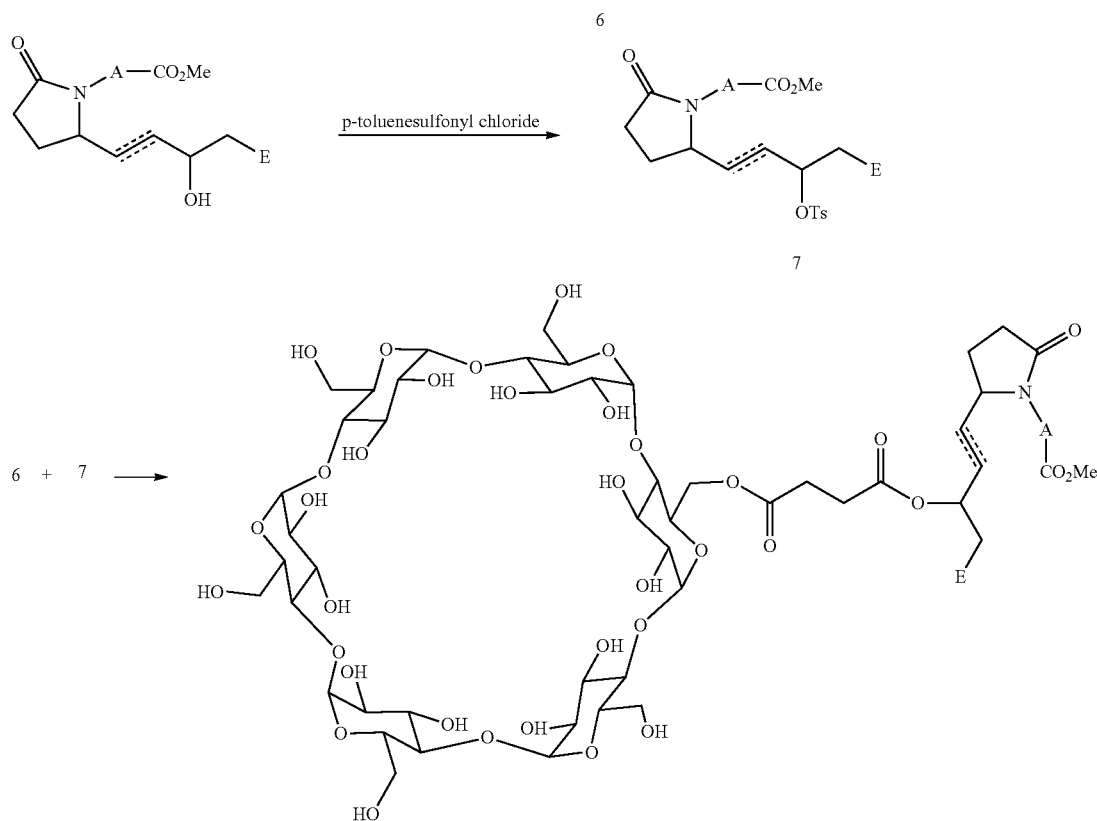

Alternatively, cyclodextrin may be attached directly to the carboxylic acid of a prostaglandin $EP_4$ agonist as shown below. This procedure is an adaptation of one disclosed by Uekama and coworkers (*J. Med. Chem.* 1997, 40, 2755-2761 and *Pharm. Pharacol.* 1996, 48, 27-31) which described preparing cyclodextrin prodrugs of anti-inflammatory carboxylic acids such as 4-biphenylacetic acid. This procedure is readily adapted to prostaglandin $EP_4$ agonists. In this procedure, the cyclodextrin is reacted with p-toluensulfonyl chloride to form the sylate 8, which is purified ion exchange chromatography followed by recrystallization from water. The hydroxyl groups of the prostaglandin are protected with THP by reaction with THPCl. Alternatively, a THP protected prostaglandin $EP_4$ agonist ester, which is frequently a late stage synthetic intermediate in the preparation of a prostaglandin $EP_4$ agonist, is saponified to give a THP protected free prostaglandin $EP_4$ agonist acid. The acid is then reacted with the cyclodextrin tosylate to give the desired prodrug, which is worked up and purified according to methods known in the art.

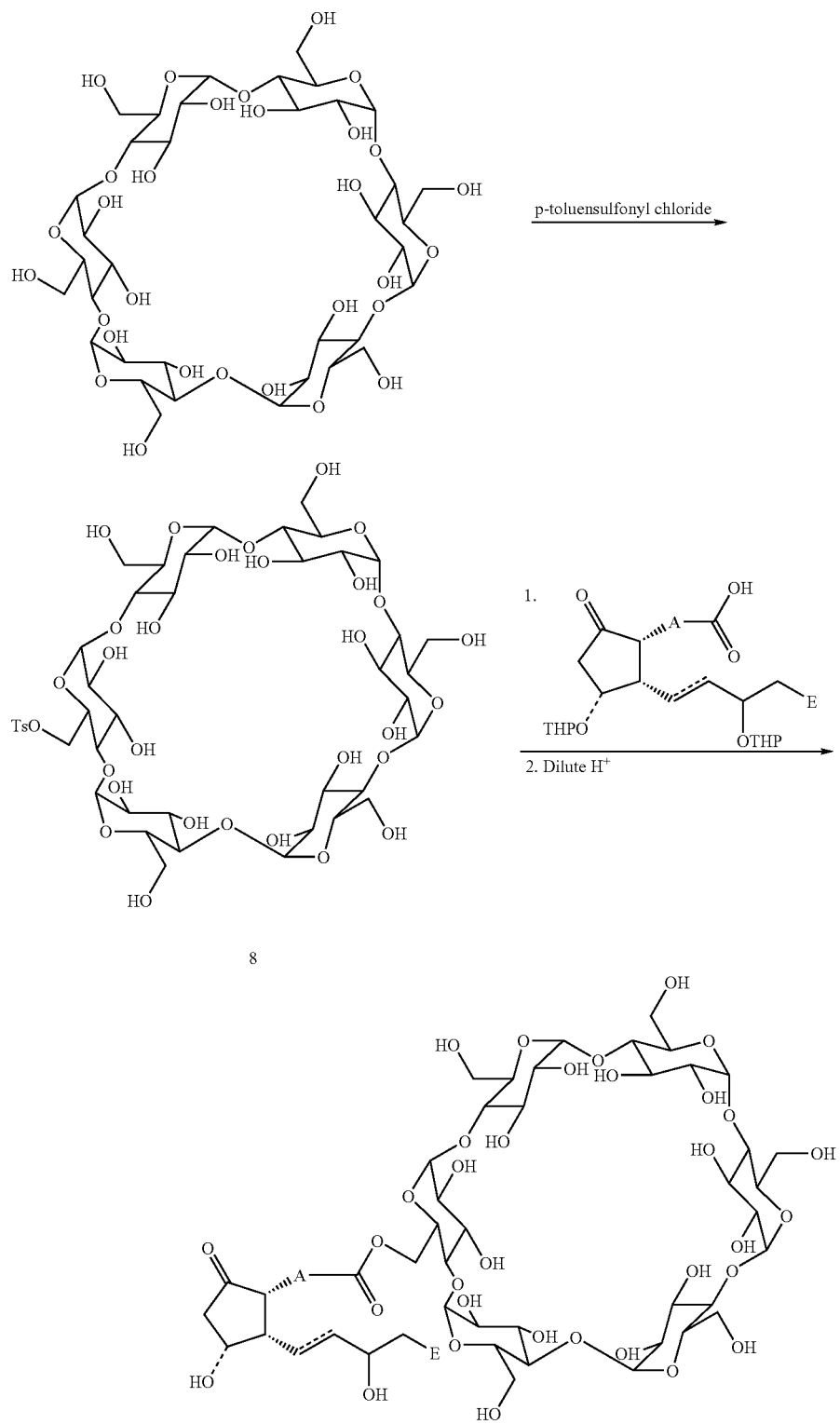

The procedure shown below may be used to line prostaglandin EP4 agonist analogs to dextran or to another carbohydrate. A procedure for the coupling of dexamethasone to dextran via a succinate linkage (McLeod et. al., *Int J. Pharm.* 1993, 92, 105-114) is readily adapted to the compounds herein. While not intending to limit the scope of the invention in any way, this procedure is most conveniently carried out with a prostaglandin $EP_4$ agonist having no free carboxylic acid (e.g. an ester) and 1 unprotected hydroxyl group. Connection to dextran to form the prodrug occurs at the free hydroxyl group. In this procedure, a hemisuccinate is formed from a hydroxyl group of a prostaglandin $EP_4$ agonist by adding it to succinic anhydride to form the hemisuccinate ester. The prostaglandin $EP_4$ agonist hemisuccinate is then reacted with 2 equivalents of 1,1-carbonyldiimidizole for 30 minutes under nitrogen. Dextran and a base such as triethylamine is added and the reaction is stirred for about 21 hours at room temperature. Any protecting groups on other hydroxyl groups may then be removed by stirring in dilute acid or another method appropriate to the protecting group being used. The carboxylic acid need not be deprotected because the ester will readily hydrolyze in vivo.

The carbohydrates used in the procedures described above are easily varied or interchanged by a person of ordinary skill in the art. For example, glucoside and glucouronide esters of the carboxylic acid of the prostaglandin $EP_4$ agonist may be prepared using the tosylate of the carbohydrate in a procedure analogous to that described for cyclodextrin.

Amino acid prodrugs are readily obtained by many methods. For example, while not intending to be limiting, one of several procedures used for the coupling of salicylic acid to a methyl ester of alanine, glycine, methionine, or tyrosine (Nakamura et. al. *J. Pharm. Pharmacol.* 1992, 44, 295-299, and Nakamura et. al. *Int. J. Pharm.* 1992, 87, 59-66) can be adapted for use with prostaglandin $EP_4$ agonists. In this procedure, an equimolar amount of dicyclohexylcarbodiimide is added at or below 0° C. to a prostaglandin $EP_4$ agonist carboxylic acid and stirred about 30 minutes. An equimolar amount of the methyl ester of the amino acid is then added and stirred overnight at room temperature to form the amide. Deprotection of any hydroxyl group can then be carried out by using dilute aqueous acid or another method, depending on the protecting group.

A number of methods of delivering a drug to the gastrointestinal tract, or desired portion thereof, via oral dosage forms, for example, solid forms, semi-solid forms, aqueous and non-aqueous liquid forms, including but not limited to, emulsions, liquid suspensions, solutions and the like, are known in the art. These include, without limitation, 1) administration, for example, oral administration, of the drug with compatible excipients, for example, conventional excipients, including, without limitation, oils, such as hydrogenated caster oil, and the like and mixtures thereof; cellulosic derivatives and starch derivatives, such as alkyl celluloses, hydroxyl alkyl celluloses, alkali metal starch carboxylates, e.g., sodium starch glycolate, and the like and mixtures thereof; and sugars and sugar derivatives and the like and mixtures thereof; so that the drug is released in the upper gastrointestinal tract, for example, esophagus, stomach, duodenum, and the like, 2) administration, for example, oral administration, of a prodrug with compatible excipients, for example, conventional excipients, for example, as noted above, with the prodrug being selected so that the drug is released in the upper gastrointestinal tract and/or lower gastrointestinal tract, as desired, 3) coating the drug and/or prodrug with, or encapsulating or impregnating the drug and/or prodrug into, a polymer designed for delivery to the lower gastrointestinal tract, 4) time released delivery of the drug and/or prodrug, 5) use of a bioadhesive system, and the like.

If desired, the presently useful compositions or dosage forms may additionally comprise other pharmaceutically acceptable excipients, such as tonicity components, buffer components, polyelectrolyte components, thickeners, fillers, diluents, flavoring agents, coloring agents, antioxidants, preservatives, such as antibacterial or antifungal agents, acids and/or bases to adjust pH, and the like and mixtures thereof. Each such additive, if present, may typically comprise about 0.0001% or less or about 0.01% or less to about 10% or more by weight of the composition. Such additives include those additives which are conventional and/or well known for use in similar pharmaceutical compositions. For example, suitable thickening agents include any of those known in the art, as for example pharmaceutically acceptable polymers and/or inorganic thickeners. Such agents include, but are not limited to, polyacrylate homo- and co-polymers; celluloses and cellulose derivatives; polyvinyl pyrrolidones; polyvinyl resins; silicates; and the like and mixtures thereof.

In one embodiment, the use of an azo-based prodrug may be employed to provide the drug in the lower gastrointestinal tract. Lower intestinal microflora are believed to be capable of reductive cleavage of an azo bond leaving the two nitrogen atoms as amine functional groups. Bacteria of the lower gastrointestinal tract also have enzymes which can digest glycosides, glucuronides, cyclodextrins, dextrans, and other carbohydrates, and ester prodrugs formed from these carbohydrates have been shown to deliver the parent active drugs selectively to the lower gastrointestinal tract.

Carbohydrate polymers including, without limitation, amylase, arabinogalactan, chitosan, chondroiton sulfate, dextran, guar gum, pectin, xylin, and the like and mixtures thereof, can be used to coat a drug and/or prodrug, or a drug and/or prodrug may be impregnated or encapsulated in the polymer. After oral administration, the polymers remain stable in the upper gastrointestinal tract, but are digested by the microflora of the lower gastrointestinal tract thus releasing the drug for therapeutic effect.

Polymers which are sensitive to pH may also be used since the lower gastrointestinal tract has a higher pH than the upper gastrointestinal tract. Such polymers are commercially available. For example, Rohm Pharmaceuticals, Darmstadt, Germany, markets pH dependent methacrylate based polymers and copolymers sold under the trademark Eudragit®, which have varying solubilities over different pH ranges based upon the number of free carboxylate groups in the polymer. Time release systems, bioadhesive systems, and other delivery systems may also be employed.

Coadministration of prostaglandin $EP_4$ agonists with one or more other, e.g., different, drugs, either in a single composition or in separate dosage forms, is also contemplated. While not intending to limit the scope of the invention in any way, other drugs which may be included in combination therapies with prostaglandin $EP_4$ agonists and their prodrugs include, but are not limited to:

Anti-inflammatory drugs, such as non-selective COX inhibitors and selective COX-2 inhibitors including, diclofenac, flurbiprofen, naproxen, suprofen, ibuprofen, ketorolac, piroxicam and the like and mixtures thereof; indoles, such as indomethacin and the like; diarylpyrazoles, such as celecoxib and the like; pyrrolo pyrroles; other agents that inhibit prostaglandin synthesis; aminosalicylates; other non-steroidal anti-inflammatory drugs, and the like and mixtures thereof;

Steroids, such as hydrocortisone, cortisone, prednisolone, prednisone, dexamethasone, medrysone, fluorometholone, estrogens, progesterones, and the like and mixtures thereof Immunomodulators, such as azathioprine, 6-mercaptopurine, cyclosporine, and the like and mixtures thereof; and Humanized monoclonal antibodies against pro-inflammatory cytokines, such as infliximab, etanercept, onercept, adalimumab, CDP571, CDP870, natalizumab, MLN-02, ISIS 2302, cM-T412, BF-5, vasilizumab, daclizumab, basiliximab, Anti-CD40L, and the like and mixtures thereof.

Such other drug or drugs are administered in amounts effective to provide the desired therapeutic effect or effects.

One useful assay for determining prostaglandin $EP_4$ activity and selectivity of compounds is described below.

Human Recombinant $EP_1$, $EP_2$, $EP_3$, $EP_4$, FP, TP, IP and DP Receptors: Stable Transfectants.

Plasmids encoding the human $EP_1$, $EP_2$, $EP_3$, $EP_4$, FP, TP, IP and DP receptors are prepared by cloning the respective coding sequences into the eukaryotic expression vector $pCEP_4$ (Invitrogen). The $pCEP_4$ vector contains an Epstein Barr virus (EBV) origin of replication, which permits episomal replication in primate cell lines expressing EBV nuclear antigen (EBNA-1). It also contains a hygromycin resistance gene that is used for eukaryotic selection. The cells employed for stable transfection are human embryonic kidney cells (HEK-293) that are transfected with and express the EBNA-1 protein. These HEK-293-EBNA cells (Invitrogen) are grown in medium containing Geneticin (G418) to maintain expression of the EBNA-1 protein. HEK-293 cells are grown in DMEM with 10% fetal bovine serum (FBS), 250 µg ml$^{-1}$ G418 (Life Technologies) and 200 µg ml$^{-1}$ gentamicin or penicillin/streptomycin. Selection of stable transfectants is achieved with 200 µg ml$^{-1}$ hygromycin, the optimal concentration being determined by previous hygromycin kill curve studies.

For transfection, the cells are grown to 50-60% confluency on 10 cm plates. The plasmid $pCEP_4$ incorporating cDNA inserts for the respective human prostanoid receptor (20 µg) is added to 500 µl of 250 mM $CaCl_2$. HEPES buffered saline ×2 (2×HBS, 280 mM NaCl, 20 mM HEPES acid, 1.5 mM $Na_2HPO_4$, pH 7.05-7.12) is then added dropwise to a total of 500 µl, with continuous vortexing at room temperature. After 30 min, 9 ml DMEM are added to the mixture. The DNA/DMEM/calcium phosphate mixture is then added to the cells, which is previously rinsed with 10 ml PBS. The cells are then incubated for 5 hr at 37° C. in humidified 95% air/5% $CO_2$. The calcium phosphate solution is then removed and the cells are treated with 10% glycerol in DMEM for 2 min. The glycerol solution is then replaced by DMEM with 10% FBS. The cells are incubated overnight and the medium is replaced by DMEM/10% FBS containing 250 µg ml$^{-1}$ G418 and penicillin/streptomycin. The following day hygromycin B is added to a final concentration of 200 µg ml$^{-1}$.

Ten days after transfection, hygromycin B resistant clones are individually selected and transferred to a separate well on a 24 well plate. At confluence each clone is transferred to one well of a 6 well plate, and then expanded in a 10 cm dish. Cells are maintained under continuous hygromycin selection until use.

Radioligand Binding

Radioligand binding studies on plasma membrane fractions prepared from cells are performed as follows. Cells washed with TME buffer are scraped from the bottom of the flasks and homogenized for 30 sec using a Brinkman PT 10/35 polytron. TME buffer is added as necessary to achieve a 40 ml volume in the centrifuge tubes. TME is comprised of 50 mM TRIS base, 10 mM $MgCl_2$, 1 mM EDTA; pH 7.4 is achieved by adding 1 N HCl. The cell homogenate is centrifuged at 19,000 rpm for 20-25 min at 4° C. using a Beckman Ti-60 or Ti-70 rotor. The pellet is then resuspended in TME buffer to provide a final protein concentration of 1 mg/ml, as determined by Bio-Rad assay. Radioligand binding assays are performed in a 100 µl or 200 µl volume.

The binding of [$^3$H] $PGE_2$ (specific activity 165 Ci/mmol) is determined in duplicate and in at least 3 separate experiments. Incubations are for 60 min at 25° C. and are terminated by the addition of 4 ml of ice-cold 50 mM TRIS-HCl followed by rapid filtration through Whatman GF/B filters and three additional 4 ml washes in a cell harvester (Brandel). Competition studies are performed using a final concentration of 2.5 or 5 nM [$^3$H] $PGE_2$ and non-specific binding is determined with $10^{-5}$ M unlabelled $PGE_2$.

For all radioligand binding studies, the criteria for inclusion are >50% specific binding and between 500 and 1000 displaceable counts or better.

The dosage of the prostaglandin $EP_4$ agonist component employed in accordance with the present invention varies over a relatively wide range and depends on a number of factors well known in the medicinal arts including, but not limited to, the weight of the individual to whom the agonist component is administered, the general health status/condition of such individual, the disease/condition sought to be treated/prevented by such administration, the severity of such disease/condition in such individual, the specific agonist component being administered, the sensitivity of such individual to the specific agonist component being administered, the mode of administration, the age of such individual, the sex of such individual, the pregnancy status of such individual, the other ongoing drug therapies being administered to such individual and the like factors.

The amount of prostaglandin $EP_4$ agonist component employed on a daily basis for each human or animal may be in a range of about 0.1 mg to about 30 mg or about 50 mg or about 100 mg or about 150 mg or about 200 mg or more. In one embodiment, such daily amount may be in a range of about 5 mg to about 150 mg or about 200 mg or more. The prostaglandin $EP_4$ agonist component may be administered in one or more doses daily, for example, once daily, twice daily, three times daily or more frequently. In one embodiment, once daily dosage is useful.

The duration of treatment with a prostaglandin $EP_4$ agonist component may vary over a wide range of times depending, for example, on factors many of which have been identified elsewhere herein. In general, the prostaglandin $EP_4$ agonist component is administered for a period of time sufficient to obtain the desired therapeutic effect or effects. The duration of treatment may be, for example, in a range of about 1 day or about 3 days or about 1 week or about 2 weeks to about 4 weeks or about 8 weeks or about 12 weeks or about 20 weeks or longer. In one useful embodiment, the duration of treatment is in a range of about 2 weeks to about 12 weeks.

The following non-limiting examples illustrate certain aspects of the present invention.

EXAMPLES 1 AND 2

A series of four (4) tablet compositions are produced using two (2) different prostaglandin $EP_4$ agonists and two (2) different prostaglandin $EP_4$ agonist prodrugs. Each of the tablet compositions is prepared as follows.

Within a dust containment area, a mixture of ingredients is prepared and blended until the mixture is uniform. The uniform mixture, having a composition as listed in the table directly below, is then used in a conventional tabletting machine to produce 100 mg tablets having such composition. The tablets may be packaged, for example, in high density polyethylene bottles, with appropriate silica gel packs, capped and labeled.

The mixtures and tablets have the following make-ups:

| | Composition | | | |
|---|---|---|---|---|
| Ingredient | 1 wt. % | 2 wt. % | 3 wt. % | 4 wt. % |
| Prostaglandin EP$_4$ Agonist 1[(1)] | 10.0 | — | — | — |
| Prostaglandin EP$_4$ Agonist Prodrug 1[(2)] | — | 10.0 | — | — |
| Prostaglandin EP$_4$ Agonist 2[(3)] | — | — | 10.0 | — |
| Prostaglandin EP$_4$ Agonist Prodrug 2[(4)] | — | — | — | 10.0 |
| Sugar | 50.0 | 50.0 | 50.0 | 50.0 |
| Excipients[(5)] | 40.0 | 40.0 | 40.0 | 40.0 |

[(1)]
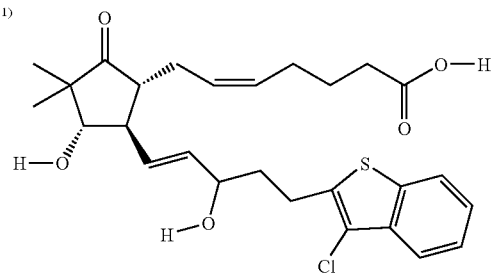

[(2)]An isopropyl ester of [(1)]above.

[(3)]
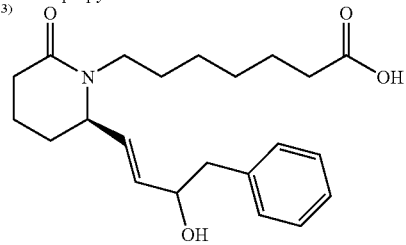

[(4)]An isopropyl ester of [(3)]above.
[(5)]A mixture of conventional pharmaceutical excipients useful, for example, as fillers, tabletting aids, bulking agents, preservatives, buffers and the like. Examples include, but are not limited to, mixtures of hydrogenated caster oil, hydroxyl ethyl cellulose, sodium starch glycolate, sorbitol and the like.

Each of the tablets that is produced in Examples 1 to 4 includes about 10 mg of the agonist or prodrug, as the case may be, which the total weight of each tablet being about 100 mg.

EXAMPLES 5 TO 8

A series of four (4) capsule compositions are produced using two (2) prostaglandin EP$_4$ agonists and two (2) prostaglandin EP$_4$ agonist prodrugs. Each of these capsule compositions is prepared as follows.

Within a dust containment area, small sugar spheres are provided. An aqueous mixture of the agonist or prodrug including a binder/sealer, such as Opadry® clear, is provided and is sprayed onto the sugar spheres using a conventional fluid bed spraying system. A second mixture including a binder/sealer, e.g., Opadry® clear, in a liquid carrier is sprayed onto the first sprayed spheres using a conventional fluid bed spraying system. This step results in agonist or prodrug loaded pellets with a sealing coat.

These pellets are coated with an aqueous mixture of triethyl citrate, talc and a methacrylic acid copolymer using a conventional fluid bed spraying system. This step results in agonist or prodrug loaded pellets with a sealing coat and an outer enteric coating. These pellets are encapsulated in natural transparent hard shell gelatin capsules. The filled capsules may be packaged, for example, in high density polyethylene bottles, with appropriate silica gel packs, capped and labeled.

The pellets with the enteric coating have the following make-ups.

| | Composition | | | |
|---|---|---|---|---|
| Ingredient | 5 wt. % | 6 wt % | 7 wt % | 8 wt % |
| Prostaglandin EP$_4$ Agonist 1[(1)] | 35.5 | — | — | — |
| Prostaglandin EP$_4$ Agonist Prodrug 1[(2)] | — | 35.5 | — | — |
| Prostaglandin EP$_4$ Agonist Prodrug 2[(3)] | — | — | 35.5 | — |
| Prostaglandin EP$_4$ Agonist Prodrug 2[(4)] | — | — | — | 35.5 |
| Sugar Spheres | 33.5 | 33.5 | 33.5 | 33.5 |
| Binder/Sealer | 11.0 | 11.0 | 11.0 | 11.0 |
| Methacrylic Acid Copolymer[(5)] | 14.8 | 14.8 | 14.8 | 14.8 |
| Talc[(6)] | 3.7 | 3.7 | 3.7 | 3.7 |
| Triethyl Citrate[(7)] | 1.5 | 1.5 | 1.5 | 1.5 |

[(1)]
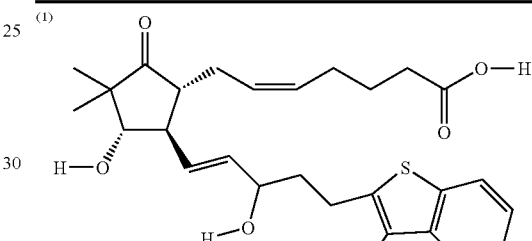

[(2)]A dextran ester of [(1)]above.

[(3)]
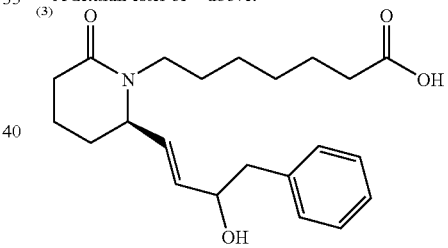

[(4)]A dextran ester of [(3)]above.
[(5)]Enteric coating composition identified as Eudragit ® L30-D55 sold by Rohm Pharmaceuticals.
[(6)]Useful as a glidant
[(7)]Useful as a plasticizer Each of the capsules that is produced in Examples 5 to 8 includes about 35.5 mg of the agonist or prodrug.

EXAMPLES 9 TO 12

Four adult humans are diagnosed with esophageal ulcers. Each of these people orally takes a tablet produced as described in Examples 1 to 4 having a different one of Compositions 1 to 4 once daily for twelve weeks. At the end of this period of time, each of the humans reports substantial relief from the esophageal ulcers. The pain and/or other symptoms of the ulcers have been reduced. In addition the ulcers have been reduced in size or substantially completely healed.

EXAMPLES 13 TO 16

Four adult humans are diagnosed with duodenal ulcers. Each of these people orally takes a tablet (produced as described in Examples 1 to 4) having a different one of Compositions 1 to 4 once daily for twelve weeks. At the end of this period of time, each of the humans reports substantial relief from the duodenal ulcers. The pain and/or other symptoms of the ulcers have been reduced. In addition the ulcers have been reduced in size or substantially completely healed.

EXAMPLES 17 TO 20

Four adult humans are diagnosed with alcohol gastropathy. Each of these people orally takes a tablet (produced as described in Examples 1 to 4) having a different one of Compositions 1 to 4 once daily for twelve weeks. At the end of this period of time, each of the humans reports substantial relief from the alcohol gastropathy. The pain and/or other symptoms of this disease have been reduced.

EXAMPLES 21 TO 24

Four adult humans are diagnosed with non-steroidal anti-inflammatory drug induced gastroenteropathy. Each of these people orally takes a tablet (produced as described in Examples 1 to 4) having a different one of Compositions 1 to 4 once daily for twelve weeks. At the end of this period of time, each of the humans reports substantial relief from the non-steroidal anti-inflammatory drug induced gastroenteropathy. The pain and/or other symptoms of this disease have been reduced.

EXAMPLES 25 TO 28

Four adult humans are diagnosed with intestinal ischemia. Each of these people orally takes a capsule (produced as described in Examples 5 to 8) containing pellets of a different one of Compositions 5 to 8 once daily for twelve weeks. At the end of this period of time, each of the humans reports substantial relief from the intestinal eschemia. The pain and/or other symptoms of this disease have been reduced.

All references, articles, patents, applications and publications set forth above are incorporated herein by reference in their entireties.

While this invention has been described with respect to various specific examples and embodiments, it is to be understood that the invention is not limited thereto and that it can be variously practiced within the scope of the following claims.

What is claimed is:

1. A method for treating a disease or condition selected from the group consisting of alcohol gastropathy and, non-steroidal anti-inflammatory drug-induced gastropathy, comprising administering to a subject in need thereof a therapeutically effective amount of a prostaglandin $EP_4$ agonist component wherein the prostaglandin $EP_4$ agonist component is selected from the group consisting of prostaglandin $EP_4$ agonists, pharmaceutically acceptable salts of prostaglandin $EP_4$ agonists, pro-drugs of prostaglandin $EP_4$ agonists selected from ethers, esters, cyclodextrins, and amino acids and mixtures thereof wherein the prostaglandin $EP_4$ agonists are selected from the group consisting of

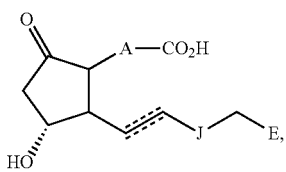

-continued

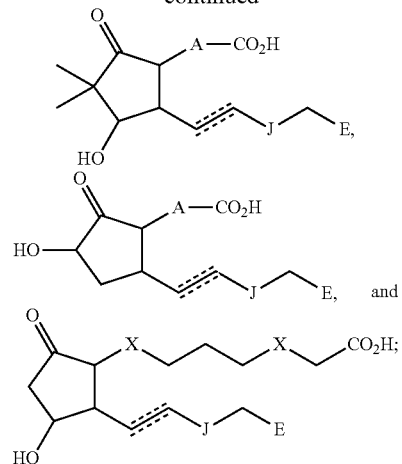

and mixtures thereof;

wherein a dashed line indicates the presence or absence of a bond;

A is $—(CH_2)_6—$, cis-$CH_2CH{=}CH—(CH_2)_3—$, $—CH_2C{\equiv}C—(CH_2)_3—$ or $—(CH_2)_m—Ar—(CH_2)_o—$ wherein Ar is interarylene, the sum of m and o is from 1 to 4;

X is S or O;

J is C=O, CHOH or $CH_2CHOH$; and

E is $C_{1\text{-}12}$alkyl, $R^2$, or $—Y—R^2$, wherein Y is $CH_2$, S or O, and $R^2$ is $CH_2$-naphthyl, $CH_2$-biphenyl, $CH_2$-(2-thienyl), $CH_2$-(3-thienyl), naphthyl, biphenyl, 2-thienyl, 3-thienyl, $CH_2$-(2-(3-chlorobenzothienyl)), $CH_2$-(3-benzothienyl), 2-(3-chlorobenzothienyl), or 3-benzothienyl.

2. The method of claim 1, wherein the prostaglandin $EP_4$ agonist component is administered to a gastrointestinal tract of the mammal.

3. The method of claim 1, wherein the disease or condition is non-steroidal anti-inflammatory drug-induced gastropathy.

4. The method of claim 1, wherein the prostaglandin $EP_4$ agonists are selected from the group consisting of

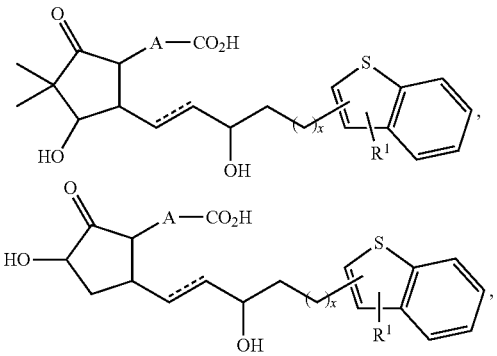

and mixtures thereof, wherein x is 0 or 1, and $R^l$ is H, chloro, fluoro, bromo, methyl, methoxy, or $CF_3$.

5. The method of claim 1, wherein the prostaglandin $EP_4$ agonists are selected from the group consisting of

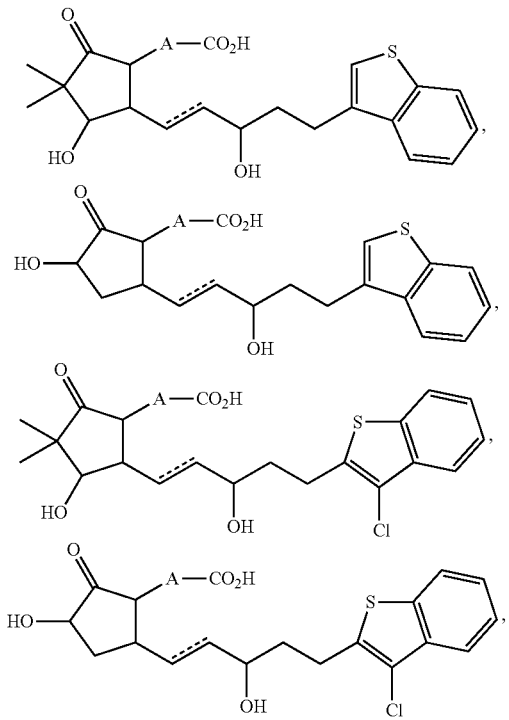

are inserted therefor.

6. The method of claim 1, wherein the prostaglandin $EP_4$ agonist component comprises at least one of

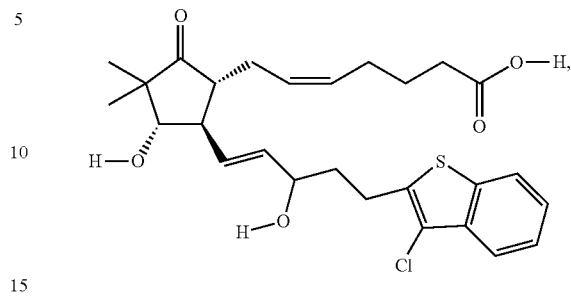

a pharmaceutically acceptable salt thereof, and a prodrug thereof.

7. A method of claim 1, wherein the prostaglandin $EP_4$ agonist component comprises a prodrug of a prostaglandin $EP_4$ agonist.

8. The method of claim 7, wherein the prodrug is an ester, ether, or amide of a carbohydrate; or the prodrug is an ester, ether, or amide of an amino acid.

9. The method of claim 7, wherein the prodrug is an amide, ester, or ether of an amino acid.

10. The method of claim 1, wherein the prostaglandin $EP_4$ agonist component comprises a glucoside ester, ether, or amide; a glucuronide ester, ether, or amide; a cyclodextrin ester, ether, or amide; or a dextran ester, ether, or amide.

* * * * *